US011793958B2

(12) United States Patent
Al Banna et al.

(10) Patent No.: US 11,793,958 B2
(45) Date of Patent: Oct. 24, 2023

(54) NEEDLE BASED PRECISION VENTURI FLOW-GENERATOR FOR POSITIVE PRESSURE VENTILATION

(71) Applicant: SPARCE LAB LLC, Dover, DE (US)

(72) Inventors: Taufiq Hasan Al Banna, Syosset, NY (US); Md Kawsar Ahmed, Rangpur (BD); Meemnur Rashid, Dacca (BD); Kaisar Ahmed Alman, Dacca (BD); Farhan Muhib, Dacca (BD)

(73) Assignee: OXYJET LIMITED, Dacca (BD)

( * ) Notice: Subject to any disclaimer, the term of this patent is extended or adjusted under 35 U.S.C. 154(b) by 0 days.

(21) Appl. No.: 17/997,607

(22) PCT Filed: Mar. 7, 2022

(86) PCT No.: PCT/US2022/019093
§ 371 (c)(1),
(2) Date: Oct. 31, 2022

(87) PCT Pub. No.: WO2022/192112
PCT Pub. Date: Sep. 15, 2022

(65) Prior Publication Data
US 2023/0277789 A1   Sep. 7, 2023

Related U.S. Application Data

(60) Provisional application No. 63/157,735, filed on Mar. 7, 2021.

(51) Int. Cl.
*A61M 16/08* (2006.01)
*A61M 16/10* (2006.01)
(Continued)

(52) U.S. Cl.
CPC ........ *A61M 16/0087* (2013.01); *A61M 16/06* (2013.01); *A61M 16/10* (2013.01)

(58) Field of Classification Search
CPC ...... A61M 11/02; A61M 11/06; A61M 15/00; A61M 15/0028; A61M 15/0093;
(Continued)

(56) References Cited

U.S. PATENT DOCUMENTS 3,068,856 A * 12/1962 Bird ...................... A61M 16/00
128/204.19
3,301,255 A * 1/1967 Thompson ............ A61M 16/16
128/200.21
(Continued)

FOREIGN PATENT DOCUMENTS

CN   208959032   6/2019
CN   111166981   5/2020
(Continued)

OTHER PUBLICATIONS

International Search Report and Written Opinion for PCT/US2022/019093, dated Aug. 1, 2022, 6pp.
(Continued)

*Primary Examiner* — Annette Dixon

(57) ABSTRACT

A flow generator for generating a mixed oxygen air flow, the flow generator including a body having a first inlet, a second inlet, an outlet, and one or more inner surfaces that define a first inner chamber in fluid communication with the first inlet and the second inlet, a second inner chamber in fluid communication with the first inner chamber, and a third inner chamber in fluid communication with the second chamber and the outlet of the body. The flow generator includes a connector disposed in the first inlet and a nozzle disposed within at least a portion of the connector and extending into the first inner chamber. The flow generator further includes an adapter engaged to the nozzle to form a fluid tight path such that the adapter connects to an external oxygen source and transports oxygen into the nozzle.

20 Claims, 11 Drawing Sheets

(51) Int. Cl.
*A61M 16/00* (2006.01)
*A61M 16/06* (2006.01)

(58) Field of Classification Search
CPC .............. A61M 16/00; A61M 16/0006; A61M 16/0012; A61M 16/0078; A61M 16/06; A61M 16/0833; A61M 16/0858; A61M 16/0875; A61M 16/101; A61M 16/104; A61M 16/107; A61M 16/12; A61M 16/127; A61M 16/14; A61M 16/16; A61M 16/20; A61M 16/201; A61M 16/207; A61M 2016/0027; A61M 2202/0208; A61M 2202/0241; A61M 2205/582; A61M 2205/583; A62B 15/00; A62B 7/12; F24F 13/26; Y10T 137/2544; Y10T 137/7852
See application file for complete search history.

(56) References Cited

U.S. PATENT DOCUMENTS

| | | | | |
|---|---|---|---|---|
| 3,463,151 A | * | 8/1969 | Neff | A61M 16/127 417/186 |
| 3,537,448 A | * | 11/1970 | Liston | A61M 16/00 128/204.25 |
| 3,630,196 A | * | 12/1971 | Bird | A61M 11/06 128/204.25 |
| 3,881,480 A | * | 5/1975 | Lafourcade | A61M 16/00 128/205.24 |
| 4,730,616 A | * | 3/1988 | Frisbie | A61M 25/01 604/164.13 |
| 5,014,694 A | * | 5/1991 | DeVries | A61M 16/12 128/205.24 |
| 5,181,508 A | * | 1/1993 | Poole, Jr. | A61M 16/0463 128/207.14 |
| 5,697,361 A | * | 12/1997 | Smith | A62B 7/12 128/204.15 |
| 9,050,434 B2 | * | 6/2015 | Faram | A61M 16/0833 |
| 2007/0056587 A1 | | 3/2007 | Travan | |
| 2008/0078385 A1 | | 4/2008 | Xiao et al. | |
| 2009/0241963 A1 | * | 10/2009 | MacMillan | A61M 39/10 128/207.14 |
| 2020/0179638 A1 | | 6/2020 | Oddo et al. | |

FOREIGN PATENT DOCUMENTS

DE 3329485 3/1985
EP 1852137 11/2007

OTHER PUBLICATIONS

Ahmed, Md. Kawsar et al., OxyJet: Design and Evaluation of a Low-Cost Precision Venturi Based Continuous Positive Airway Pressure (CPAP) System. arXiv:2106.00981v1 [physics, med-ph] Jun. 2, 2021.

* cited by examiner

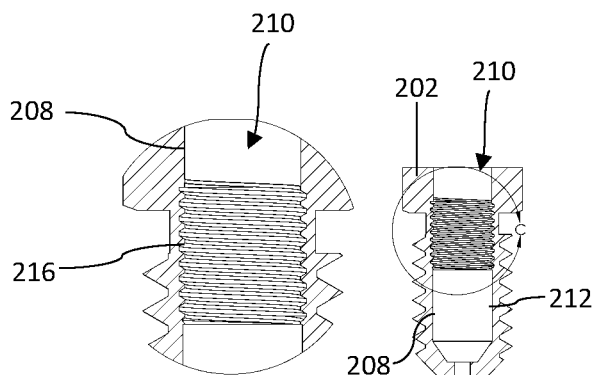
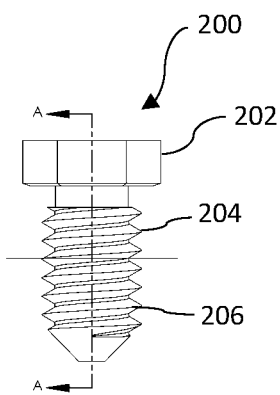
FIG. 11C  FIG. 11B  FIG. 11A
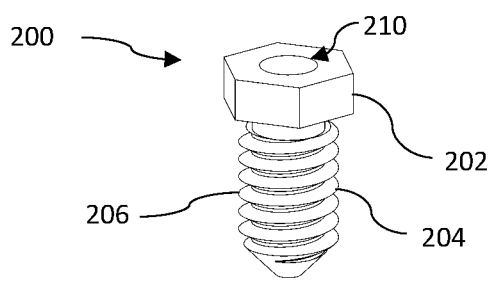
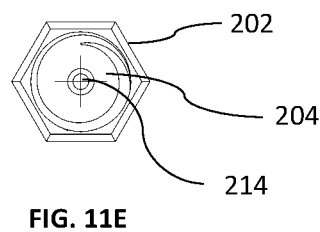
FIG. 11D  FIG. 11E
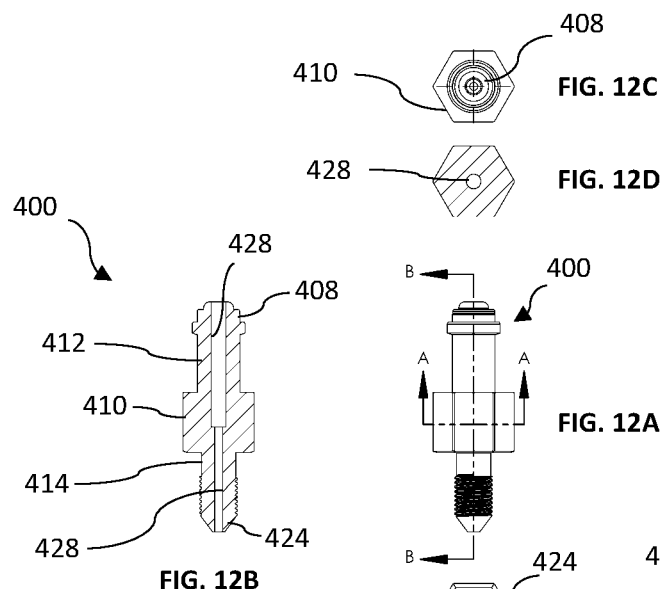
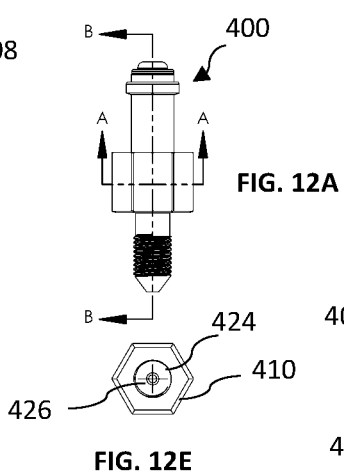
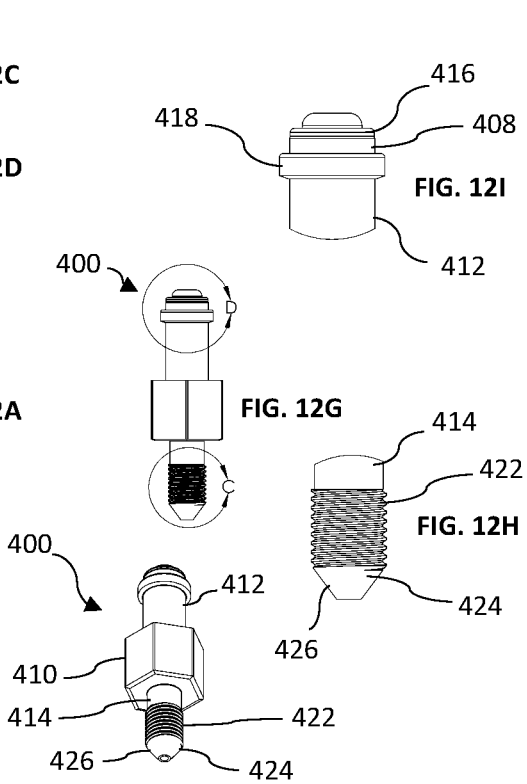

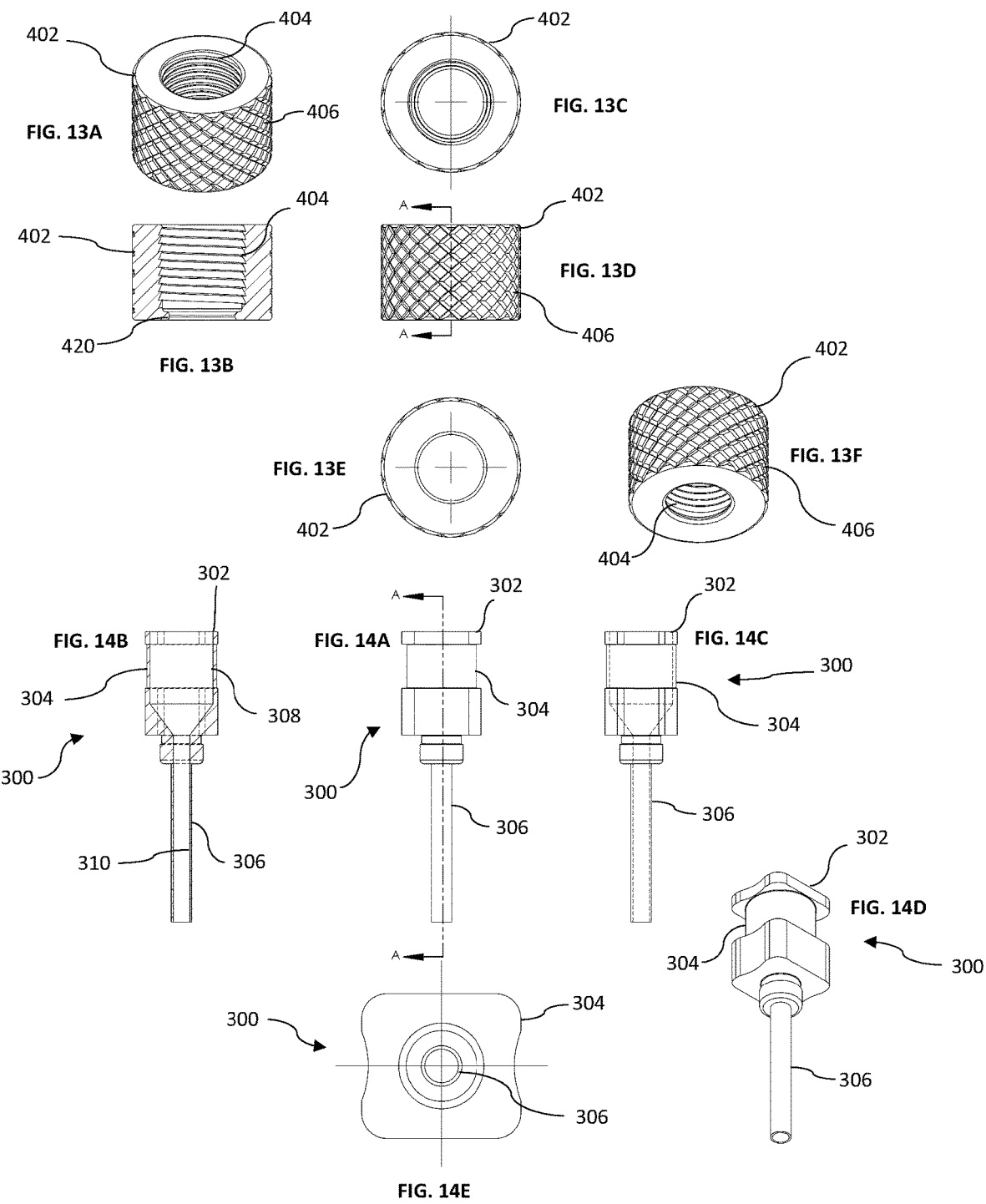

NEEDLE BASED PRECISION VENTURI FLOW-GENERATOR FOR POSITIVE PRESSURE VENTILATION

CROSS-REFERENCE

This application claims priority to International Patent Application No. PCT/US2022/19093, filed on Mar. 7, 2022, and U.S. Provisional Application No. 63/157,735, filed on Mar. 7, 2021, the contents of which each application are incorporated herein by reference in their entirety.

TECHNICAL FIELD

This disclosure generally relates to a flow generator for a respiratory apparatus and more specifically it relates to a continuous positive airway pressure (CPAP) flow generator which can generate and deliver a pressurized airflow by mixing oxygen and surrounding environmental room air.

BACKGROUND

Continuous positive airway pressure (CPAP) flow generators deliver a pressurized airflow to improve the oxygen saturation level by opening blocked or restricted airways. For example, CPAP flow generators are used to treat obstructive sleep apnea patients or hypoxic patients that have a lower blood oxygen saturation (% $SpO_2$). CPAP flow generators can also be used for treating hypoxaemic respiratory failure observed in patients suffering from acute respiratory illnesses such as COVID-19. CPAP flow generators can provide respiratory distress relief because air flow generated by the flow generators maintains a greater airway pressure in the upper respiratory tract than the surrounding external atmospheric pressure. This increased airway pressure helps to reinflate collapsed alveoli in the patient's respiratory system and helps to increase the patient's blood oxygen saturation. Additionally, the increased airway pressure helps to keep alveoli and other parts of the respiratory system from collapsing.

The usage of CPAP flow generators is a known treatment for individuals suffering from respiratory distress, such as but not limited to, hypoxaemic respiratory failure, sleep apnea, and pneumonia. Furthermore, since late 2019, the world has been combating the COVID-19 pandemic which is a disease that attacks the respiratory system to cause shortness of breath, chest pain, fever, dry cough, diarrhea, loss of taste, loss of smell and other such symptoms. Accordingly, CPAP flow generators have been used as an intermediate treatment step for hypoxic COVID-19 patients.

SUMMARY

While known CPAP flow generators can generate pressurized air flow, these known flow generators often experience various challenges and limitations during operation. For example, these known CPAP flow generators typically include an electrically powered blower or centrifugal fan that draws environmental air into the device to generate the pressurized air flow output by the device. As such, known CPAP flow generators require an electricity source to power the electrical components of the device. Furthermore, known CPAP flow generators are also not configured to receive pure oxygen ($O_2$) gas from an external source and mix the $O_2$ gas with external environmental air to generate an $O_2$ rich air flow output by the flow generator. Thus, in order to use known CPAP flow generators to increase a patient's fraction of inspired oxygen ($FiO_2$), these CPAP flow generators require additional connections added to the air inlet, such as a T-connector or other such connector, to deliver pure $O_2$ gas and enable the CPAP device to mix pure $O_2$ gas with drawn in environmental air. As a result, known CPAP flow generators cannot provide up to 100% $FiO_2$ and are not appropriate devices for use in treating hypoxic COVID-19 patients.

Existing CPAP flow generators also have a complex manufacturing process and have high maintenance costs that can limit accessibility and use of the flow generators to treat patients in less developed areas.

This application discloses embodiments of a flow generator and embodiments of components for a flow generator. At least some of these embodiments resolve, or at least partially resolve, one or more of the above challenges.

One embodiment of a flow generator of the disclosure for generating an oxygen rich air flow has a body, a connector disposed in the body, a nozzle disposed in the connector and at least a portion of the body, and an adapter disposed in the connector. The body includes a first inlet, a second inlet, an outlet, and one or more inner surfaces that define a first inner chamber in fluid communication with the first inlet and the second inlet, a second inner chamber in fluid communication with the first inner chamber, and a third inner chamber in fluid communication with the second chamber and the outlet of the body. The connector is disposed in the first inlet and connected to the body. The connector includes one or more inner surfaces that define a connector inner chamber and a connector bore extending into the inner chamber. The nozzle is disposed within at least a portion of the connector inner chamber and extends into the first inner chamber. The adapter extends through the connector bore into the connector inner chamber and the adapter is sealingly engaged to the nozzle to form a fluid tight flow path through the adapter and the nozzle. The adapter is configured to connect to and receive a first pressurized oxygen supply from a primary oxygen source and transport the first pressurized oxygen supply into the nozzle.

This application is defined by the appended claims. The description summarizes aspects of exemplary embodiments and should not be used to limit the claims. Other implementations are contemplated in accordance with the techniques described herein, as will be apparent upon examination of the following drawings and detailed description, and such implementations are intended to be within the scope of this application.

BRIEF DESCRIPTION OF THE DRAWINGS

FIGS. 11A-11E show different perspective views and cross-sectional views of the connector taken along line A-A.

FIGS. 12A-12I show different perspective views and cross-sectional views of the adapter taken along lines A-A and B-B.

FIGS. 13A-13F show different perspective views and a cross-sectional view of the rotatable knob taken along line A-A.

FIGS. 14A-14E show different perspective views and cross-sectional view of the nozzle taken along line A-A.

DETAILED DESCRIPTION

Figure 1:
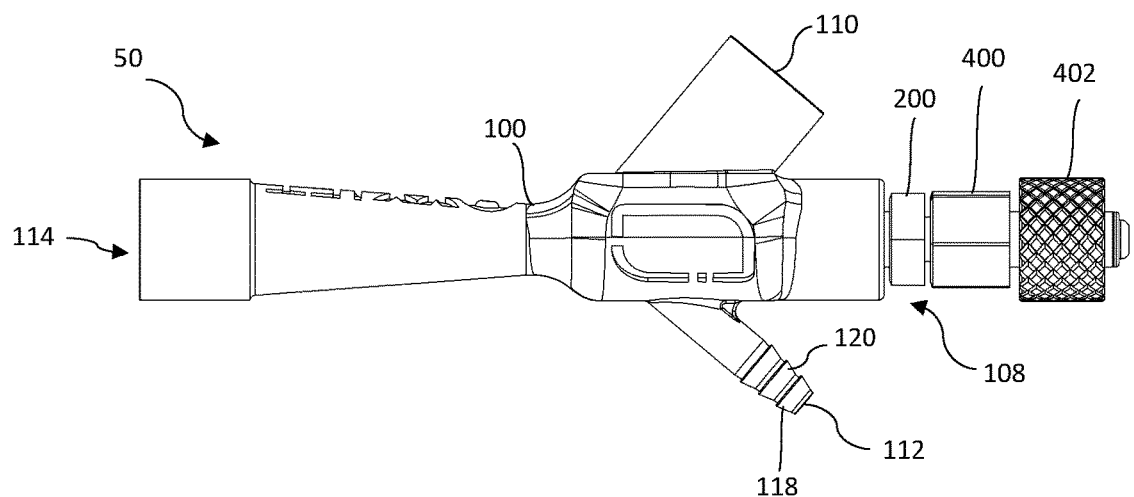
FIG. 1 is a side view of one embodiment of the flow generator of the disclosure.
Figure 2:
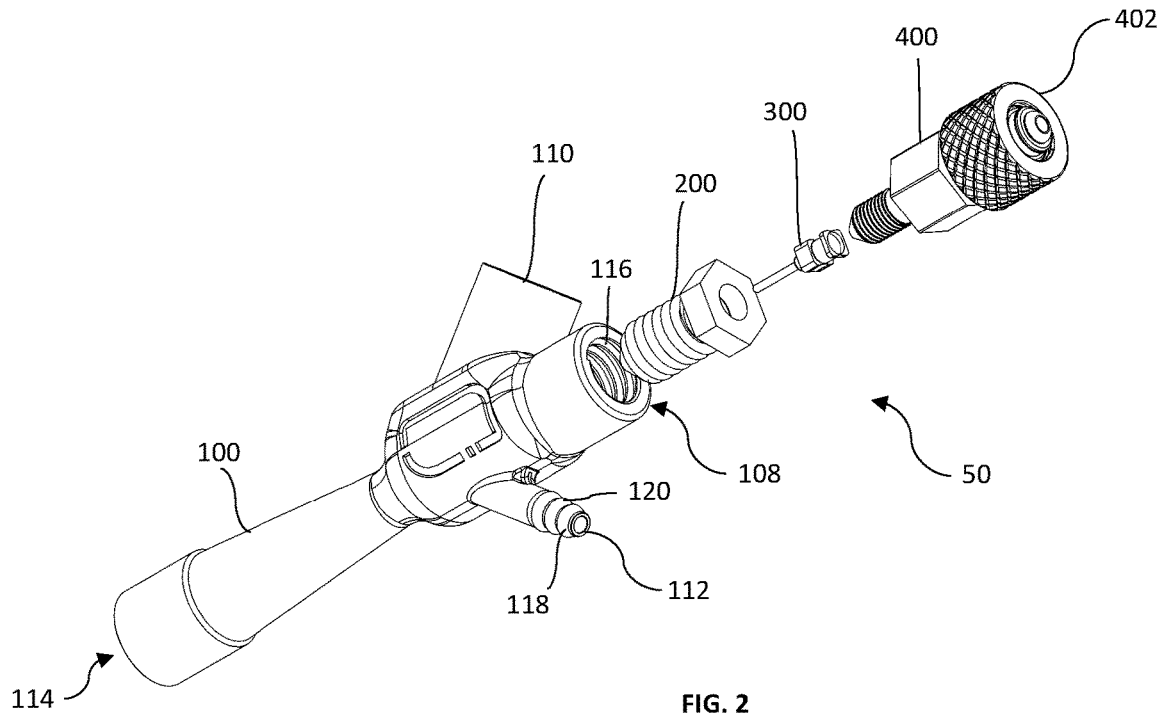
FIG. 2 is an exploded perspective view of the flow generator of FIG. 1.
Figure 3:
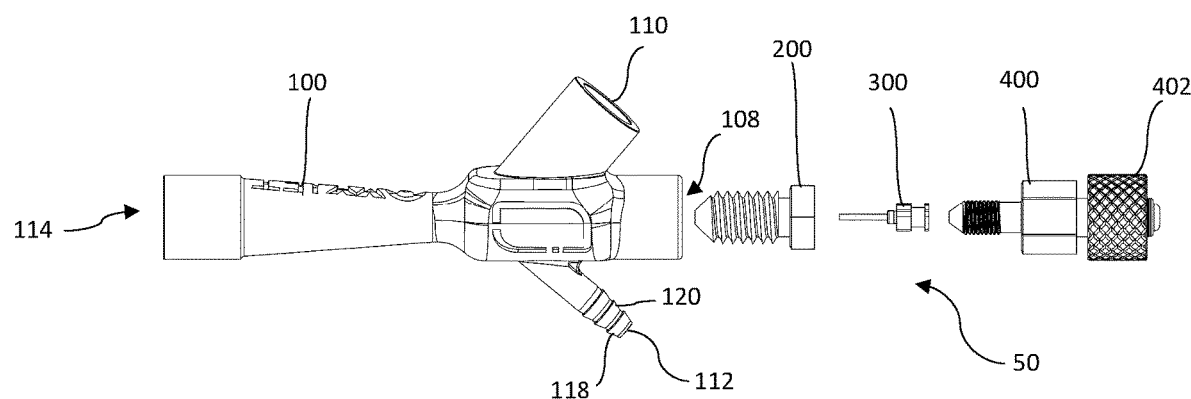
FIG. 3 is an exploded side view of the flow generator of FIG. 1.
Figure 4B:
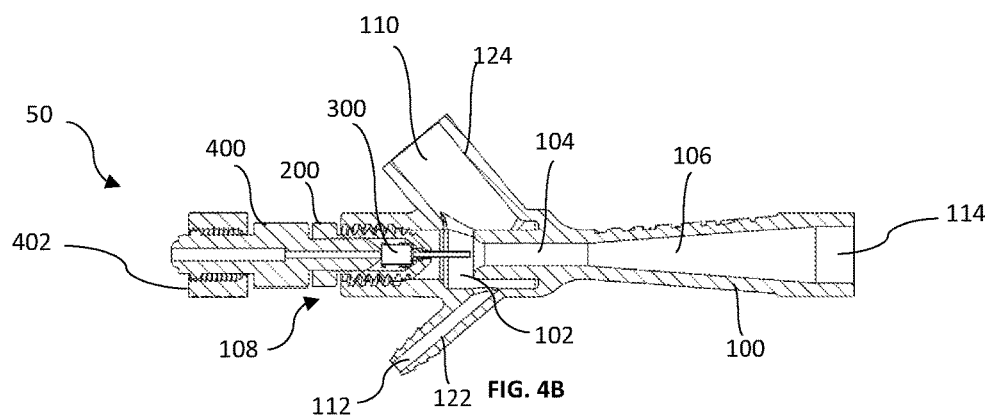
FIG. 4B is a cross-sectional view of the flow generator of FIG. 4A taken along line B-B.
Figure 4A:
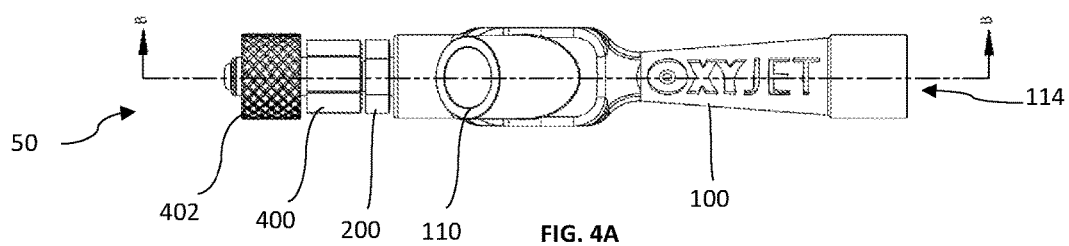
FIG. 4A is a top view of the flow generator of FIG. 1.
Figure 5A:
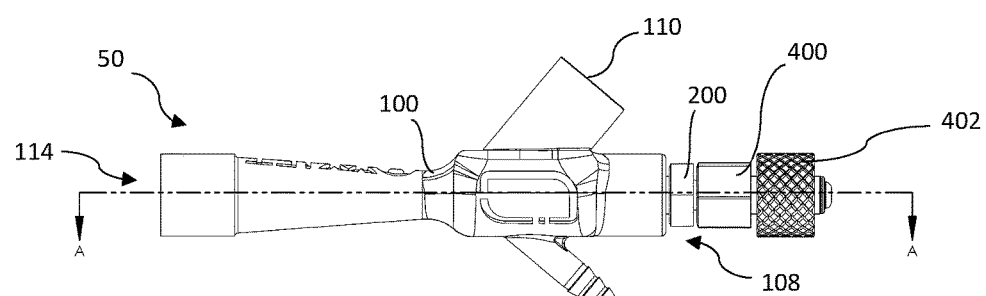
FIG. 5A is a side view of the flow generator of FIG. 1.
Figure 5B:
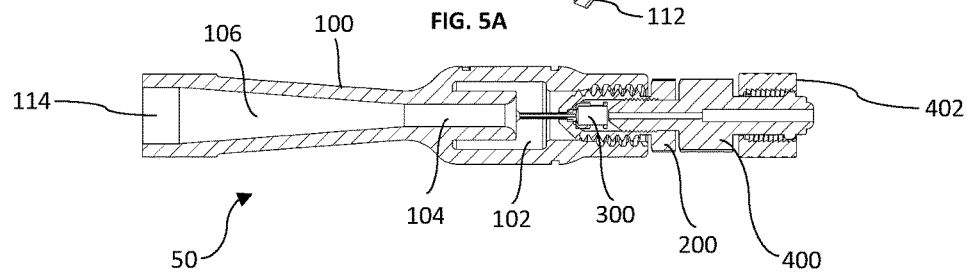
FIG. 5B is a cross-sectional view of the flow generator of FIG. 5A taken along line A-A.

The description that follows describes, illustrates, and exemplifies one or more embodiments of the disclosure in accordance with its principles. This description is not provided to limit the exemplary embodiments described herein, but rather to explain and teach the principles of the embodiments to enable one of ordinary skill in the art to understand these principles and, with that understanding, be able to apply them to practice not only the embodiments described herein, but also other embodiments that may come to mind in accordance with these principles.

The scope of the disclosure is intended to cover all such embodiments that may fall within the scope of the appended claims, either literally or under the doctrine of equivalents. The specification describes exemplary embodiments which are not intended to limit the claims. Features described in the specification, but not recited in the claims, are not intended to limit the claims.

It should be noted that in the description and drawings, like or substantially similar elements may be labeled with the same reference numerals. However, sometimes these elements may be labeled with differing numbers, such as, for example, in cases where such labeling facilitates a clearer description. Additionally, the drawings set forth herein are not necessarily drawn to scale, and in some instances, proportions may have been exaggerated to better illustrate certain features. Such labeling and drawing practices do not necessarily implicate an underlying substantive purpose.

Some features may be described using relative terms such as top, bottom, vertical, rightward, leftward, first, second, and the like. These relative terms are only for reference with respect to the appended Figures. These relative terms are not meant to limit the disclosed embodiments. More specifically, it is contemplated that the flow generator depicted in the appended Figures will be oriented in various directions in practice and that the relative orientation of features will change accordingly.

As stated above, the disclosure is intended to be taken as a whole and interpreted in accordance with the principles of the disclosure as taught herein and understood by one of ordinary skill in the art.

The disclosure describes a flow generator that creates a pressurized air flow by mixing pressurized $O_2$ gas with environmental air. The flow generator receives the pressurized $O_2$ from an external $O_2$ source (e.g., pressurized gas cylinder) or an $O_2$ medical supply line. A nozzle housed within a body of the flow generator defines a restricted or constricted air passage in the flow generator flow pathway. This constricted passage generates an increase in velocity of the $O_2$ molecules flowing from the pressurized external $O_2$ source through the flow generator. As such, the flow generator of the disclosure generates a low-pressure zone in within the flow generator body that has an air pressure that is less than the atmospheric pressure of the surrounding environmental or room air. The lower air pressure of the low-pressure zone enables the flow generator to draw or entrain surrounding environmental room air into the flow generator body. The drawn in environmental air mixes with the pressurized, high velocity $O_2$ gas to form a pressurized homogenous $O_2$ rich air flow inside the flow generator. The flow generator of the disclosure can output or otherwise deliver the generated pressurized homogenous $O_2$ rich airflow to a patient using a dual-port CPAP mask, a helmet, or other such breathing apparatus. In various embodiments, the flow generator of the disclosure can generate and deliver a desired Positive End Expiratory Pressure (PEEP) that can maintain a positive pressure flow at the end of exhalation to help maintain the patient's airway pressure above the surrounding atmospheric level by exerting pressure that opposes passive emptying of the patient's lungs.

The flow generator of the disclosure uses certain venturi jet mixing principles to generate the pressurized homogenous $O_2$ rich air flow that can be used for CPAP therapy or treatment of other respiratory conditions. The flow generator of the disclosure is configured to generate the pressurized homogenous $O_2$ rich air flow without the use of electricity. That is, the flow generator of the disclosure utilizes the incoming flow of the pressurized primary $O_2$ gas (and not any electrically powered components) to generate the venturi mixing jet that draws environmental air into the flow generator. The flow generator of the disclosure is configured as a portable device that can be used to generate a pressurized homogenous $O_2$ rich air flow without needing to be "plugged in." Accordingly, the flow generator of the disclosure enables use of the device in a wide variety of clinical setups and can be used in remote locations where electricity is unavailable or unstable.

In various embodiments, the flow generator of the disclosure can be optimized by using different sized nozzles to define at least a portion of the constricted passage of the flow generator. In various embodiments, the nozzle is configured as a removable component of the flow generator such that the flow generator can be customized based on the desired application to generate a flow rate between 60 Liters per Minute (LPM) to 120 LPM. The nozzle of the flow generator can also be customized and/or optimized to maintain a constant PEEP pressure within an operating range of 5 to 20 cmH$_2$O. Furthermore, in various embodiments, the flow generator of the disclosure can be configured to receive pressurized O$_2$ from a secondary source (and received via a secondary inlet) such that the FiO$_2$ level of the device output can be increased up to a 100% FiO$_2$ level without significantly changing the total output flow of the device.

The flow generator of the disclosure is configured or otherwise designed such that the device is compatible with existing medical ventilator breathing circuits, adapters, tubes, non-vented CPAP masks, helmets, PEEP valves, and other respiratory apparatus components. Compatibility with existing breathing apparatus circuits and the availability of attachments and accessories is a tremendous advantage of the flow generator. For example, to generate the pressurized homogenous O$_2$ rich air flow the flow generator of the disclosure only requires a connection to an external pressurized O$_2$ source. Put differently, the flow generator of the disclosure uses the incoming pressurized O$_2$ gas to create a venturi mixing jet that draws external air into the flow generator to mix with the pressurized O$_2$ gas and produce a homogenous O$_2$ rich air flow. As such, the flow generator of the disclosure generates the homogenous O$_2$ rich air flow without the need for electricity. Additionally, the external pressurized O$_2$ flow rate is used to control the overall flow rate of the homogenous O$_2$ rich air flow generated by the flow generator. As such, the flow generator of the disclosure provides an economical and easy to operate flow generator that can be used by everyone.

Referring now to the figures, FIGS. 1-5B and 16 illustrate one example embodiment of the flow generator of the disclosure, identified as flow generator 50. In the illustrated example, the flow generator 50 includes a flow generator body 100 (sometimes referred to herein as body for brevity), a body connector 200 (sometimes referred to herein as connector for brevity) suitably connected to the body 100, a primary nozzle 300 (sometimes referred to herein as nozzle for brevity) disposed in at least a portion of the connector 200, and an adapter 400 sealingly engaged with the nozzle 300 and threadably engaged with the connector 200. In the illustrated example, the adapter 400 includes a rotatable knob 402 suitably connected to the adapter 400 and configured to removably connect the flow generator 50 to a flow meter or regulator (not shown) connected to an external pressurized O$_2$ supply (not shown) or other such pressurized gas source.

In the illustrated example, the flow generator 50 generates a driving flow of gas through the body 100 to produce a homogenous O$_2$ rich air flow output by the flow generator 50. The body 100 includes multiple inner and outer surfaces that define inlets, outlets, and interior or inner chambers that along with the nozzle 300, form a constricted flow path through the body 100 to generate the desired driving flow of O$_2$ rich air output by the flow generator 50. As best shown in the cross-sectional views of FIGS. 4B, and 5B, the body 100 includes multiple inner surfaces (not labeled for clarity) that define a first inner chamber 102 (sometimes referred to herein as a suction chamber), a second inner chamber 104 (sometimes referred to herein as a mixing chamber) in fluid communication with the first inner chamber 102, and a third inner chamber 106 (sometimes referred to herein as a diffuser chamber) in fluid communication with the second inner chamber 104. In the illustrated example, the plurality of inner surfaces of the body 100 are configured such that the inner chambers 102, 104, and 106 are in fluid communication with each other and define a fluid flow pathway through the body 100.

In the illustrated example, the inner and outer surfaces of the body 100 also define a first inlet 108 (sometimes referred to herein as the primary O$_2$ inlet) at a first end of the body 100, a flow generator outlet 114 (sometimes referred to herein as the outlet) at a second end of the body 100 opposite the first end, a second inlet 110 (sometimes referred to herein as the environmental air inlet) disposed between the primary O$_2$ inlet 108 and the outlet 114, and a third inlet 112 (sometimes referred to herein as the secondary O$_2$ inlet) disposed between the primary O$_2$ inlet 108 and the outlet 114. However, while the illustrated example of the flow generator 50 includes three inlets and one outlet, it will be understood that the body can be configured to include a different number of inlets and/or outlets (e.g., a fewer or greater number).

In the illustrated example, the primary O$_2$ inlet 108, environmental air inlet 110, and secondary O$_2$ inlet 112 are each connected to and in fluid communication with the suction chamber 102 of the body 100. As such, a primary source of pressurized O$_2$ (sometimes referred to herein as the driving gas flow) flows into the body 100 via the primary O$_2$ inlet 108. The velocity of the incoming pressurized O$_2$ generates a low-pressure region in the suction chamber 102 that causes the flow generator 50 to draw or otherwise entrain surrounding environmental air into the flow generator 50. More specifically, the low-pressure region generated in the suction chamber 102 causes the flow generator 50 to draw surrounding environmental air into the suction chamber 102, via the environmental air inlet 110. As such, the incoming pressurized O$_2$ and entrained environmental air combine with each other in the suction chamber 102 and mix with one another in the mixing chamber 104 to form the pressurized homogenous O$_2$ rich air mixture. As discussed herein, the pressurized homogenous O$_2$ air mixture continues to flow from the mixing chamber 104, through the diffuser chamber 106, and flow out of the body 100 via the outlet 114.

In the illustrated example, the mixing chamber 104 has a first chamber diameter that is constant along a length of the mixing chamber 104. As such, the mixing chamber 104 defines a portion of the flow generator 50 having a constant diameter and constant cross-sectional area along the mixing chamber length. In the illustrated example, the constant cross-sectional area of the mixing chamber 104 is configured to enable the incoming pressurized O$_2$ and environmental air to mix and form the homogenous O$_2$ rich gas mixture. It will be understood that while the mixing chamber 104 has a constant diameter along the chamber length, different diameters (i.e., increasing or decreasing) are possible.

In the illustrated example, the diffuser chamber 106 defines an area of the flow generator 50 having a changing (e.g., increasing or decreasing) diameter along a length of the diffuser chamber 106. For example, the diffuser chamber 106 has a second chamber diameter defined adjacent the mixing chamber 104 and a third chamber diameter adjacent the outlet 114. In the illustrated example, the first chamber diameter of the mixing chamber 104 and the second chamber diameter of the diffuser chamber 106 are substantially equal to or similar (e.g., within manufacturing tolerances) and the third chamber diameter of the diffuser chamber 106 is larger than the first and second diameters. As such, the diffuser chamber 106 has an increasing cross-sectional area from a chamber first end adjacent the mixing chamber 104 to a chamber second end adjacent the outlet 114. In the illustrated example, the increasing cross-sectional area of the diffuser chamber 106 is configured to decelerate the flow velocity of the homogenous $O_2$ rich gas and induce a pressure recovery of the gas flow before the homogenous gas flow exits the flow generator 50.

Figure 6:
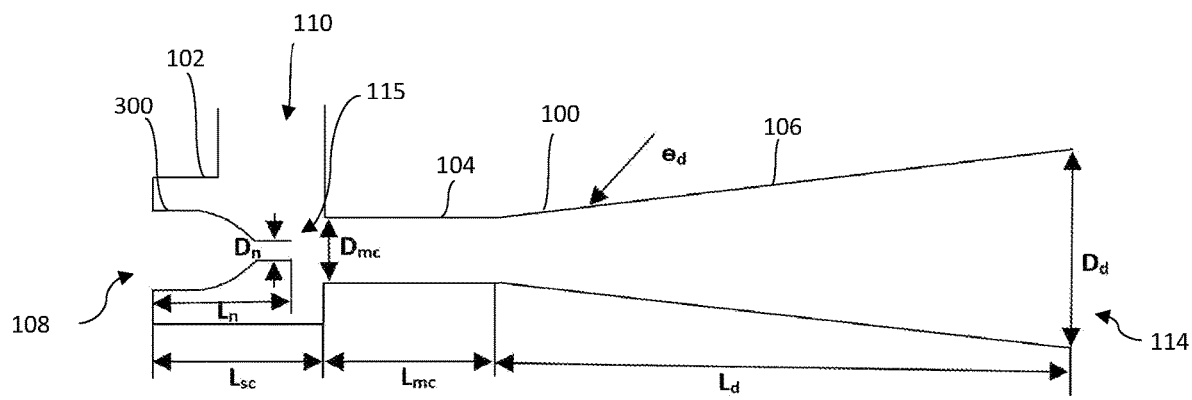
FIG. 6 is a schematic view of the body of the flow generator of FIG. 1.
Figure 7:
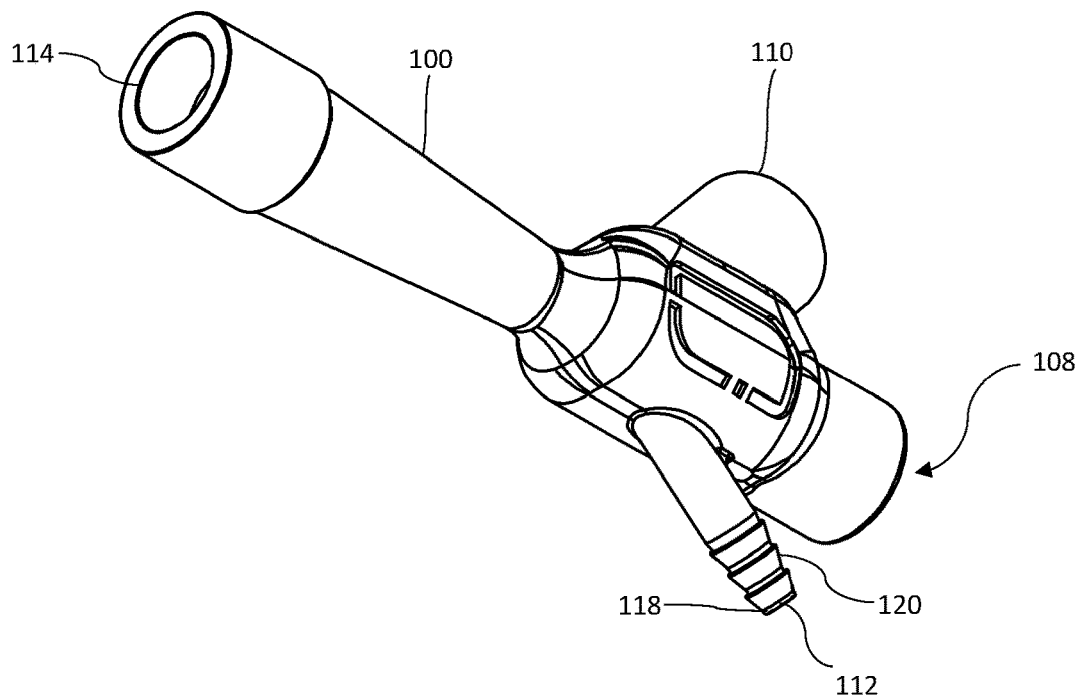
FIG. 7 is a perspective view of the body of the flow generator of FIG. 1 showing the primary $O_2$ inlet, the environmental air inlet, the secondary $O_2$ inlet, and the outlet.
Figure 8:
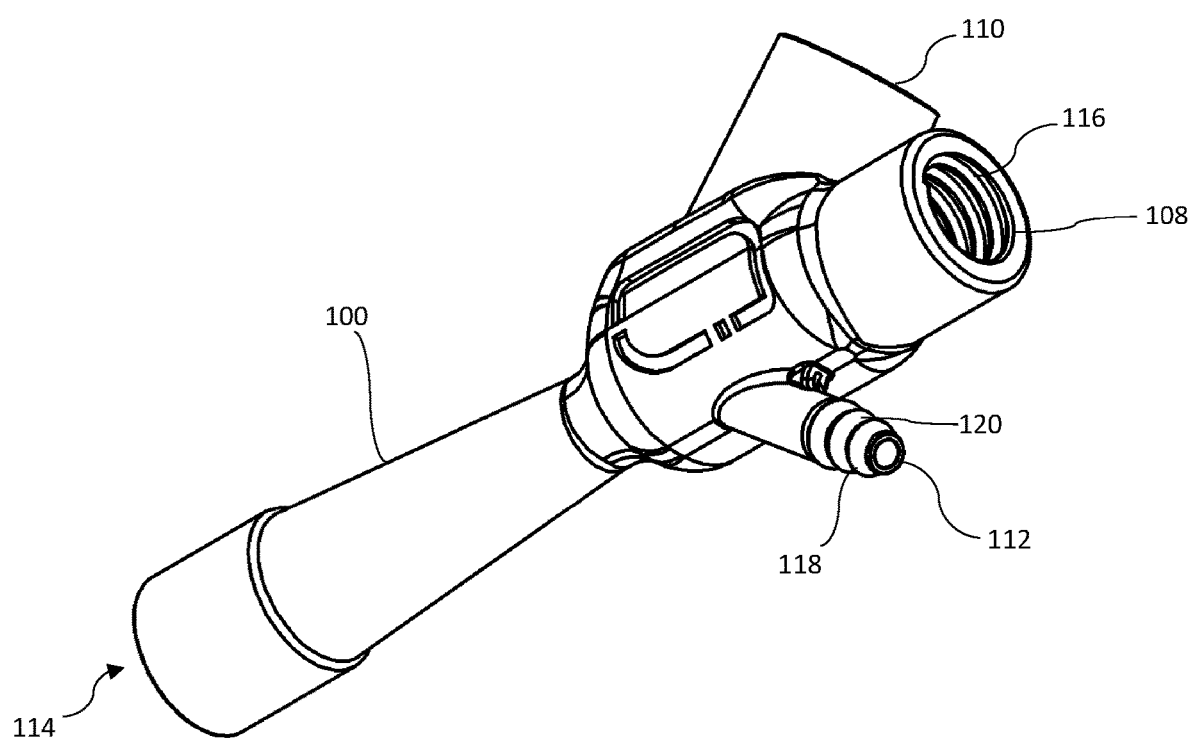
FIG. 8 is a perspective view of the body of the flow generator of FIG. 1 showing the primary $O_2$ inlet, the environmental air inlet, the secondary $O_2$ inlet, and the outlet.
Figures 9A, 9B, 9C:
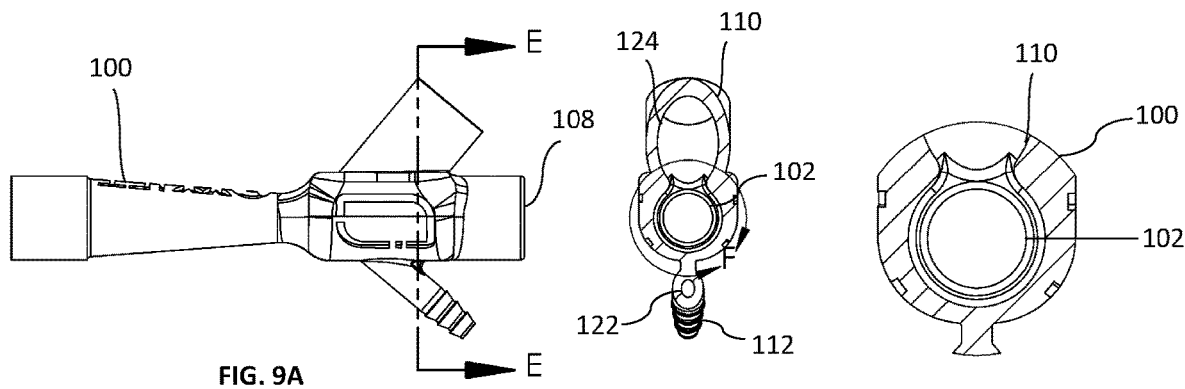
FIGS. 9A-9C shows a side view and enlarged partial cross-sectional views of the flow generator body taken along the line E-E.
Figures 10A, 10B, 10C, 10D:
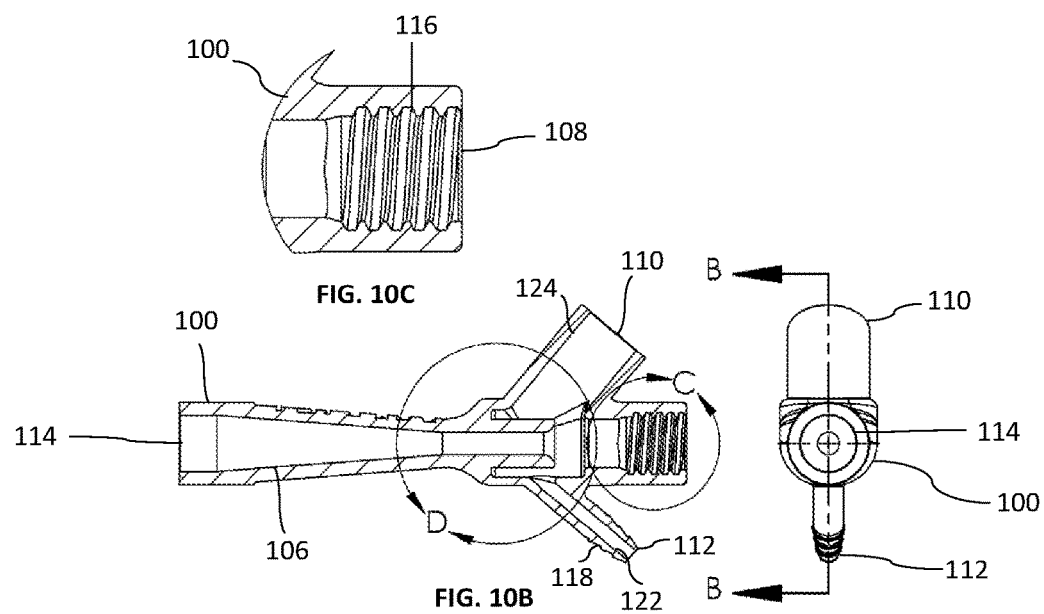
FIGS. 10A-10D shows a front view, a cross-sectional view of the flow generator body taken along line B-B and enlarged partial cross-sectional views of the flow generator body.

As shown schematically in FIG. 6, the body 100 includes the certain parameters that can be specified during the fabrication process such that the flow generator 50 produces a desired output. In the illustrated example, the body 100 includes the following parameters: (1) suction chamber length ($L_{sc}$); (2) mixing chamber length ($L_{mc}$); (3) mixing chamber diameter ($D_{mc}$); (4) diffuser chamber length ($L_d$); (5) diffuser expansion angle ($\Theta_d$); and (6) outlet diameter ($D_d$). In the illustrated example, these parameters, along with certain parameters of the nozzle 300, can be optimized or otherwise configured such that the flow generator 50 forms the constricted flow path through the body 100 to generate a desired homogenous $O_2$ rich gas flow. Furthermore, it will be understood that while the body 100 is generally described as a circular or cylindrical structure, other shapes and geometries of the body are possible.

In the illustrated example, the body 100 is configured such that upon assembly of the flow generator 50 at least a portion of the nozzle 300 is positioned within the suction chamber 102 to define a gap 115 between the outlet of the nozzle 300 and the inlet of the mixing chamber 104. In various embodiments and as best illustrated schematically in FIG. 6, the length of the gap 115 is defined by subtracting the nozzle length ($L_n$) from the suction chamber length $L_{sc}$ (i.e., $L_{sc}$-$L_n$). As such, the length of the gap 115 defined between the outlet of the nozzle 300 and inlet of the mixing chamber 104 can be optimized based on certain desired flow characteristics. That is, certain dimensions of the suction chamber length and/or nozzle length can be optimized to form or otherwise define the desired gap between the nozzle 300 and the mixing chamber 104.

Furthermore, a ratio between the gap 115 and mixing chamber diameter $L_{gap}/D_{mc}$ can be optimized to provide a desired performance of the flow generator 50. In one non-limiting example a $L_{gap}/D_{mc}$ ratio between 0.25 and 1.5 is used, however other ratios between these dimensions are possible. In the illustrated example, other parameters can be optimized to provide the desired performance, such as but not limited to, specifying a desired ratio between the mixing chamber diameter ($D_{mc}$) and nozzle diameter (Do) (e.g., $D_{mc}/D_n$ between 8 and 14), a ratio of mixing chamber length ($L_{mc}$) and mixing chamber diameter ($D_{mc}$) (e.g.,., $L_{mc}/D_{mc}$ between 4 and 12), and diffuser expansion angle $\Theta_d$ (e.g., between 2° to 6°).

As best shown in FIGS. 1-5B, 7, and 8, the body 100 is fabricated as a unitary structure that includes the primary $O_2$ inlet 108, environmental air inlet 110, secondary $O_2$ inlet 112, and outlet 114. The primary $O_2$ inlet 108 is defined at a first end of the body 100 and the outlet 114 defined at a second end of the body 100 opposite the first end. The environmental air inlet 110 and secondary $O_2$ inlet 112 are each disposed between the primary $O_2$ inlet 108 and the outlet 114 and extend radially outward from the body 100. In one non-limiting example, the body 100 is fabricated using a three-dimensional printing (3D) process that enables fabrication of the body 100 out of a suitable plastic or polymeric material. More specifically, in one non-limiting example, the body 100 is fabricated from a medical grade and biocompatible plastic material such as, but not limited to, polylactic acid (PLA), thermoplastic polyurethane (TPU) acrylonitrile butadiene styrene (ABS), polypropylene (PP), and polyvinylchloride (PVC), however it will be understood that other materials are possible.

Furthermore, 3D printing of the body 100 enables for specification and customization of certain dimensions and other parameters of the body 100 to optimize a desired performance (e.g., flow rate, or output) of the flow generator 50. It will be understood that while 3D printing can be used to fabricate the body, other manufacturing processes such as injection molding, machining, and the like can be used to fabricate the body and other components of the flow generator 50.

In the illustrated example, the environmental air inlet 110 is disposed between the primary $O_2$ inlet 108 and the outlet 114 and extends radially outward from the body 100. The environmental air inlet 110 is oriented or otherwise configured to form an angle of approximately 55° (e.g., within manufacturing tolerances) with the body 100, however other angles and configurations of the environmental air inlet are possible. The environmental air inlet 110 is configured with a specified diameter (e.g., between 10 mm to 20 mm) such that sufficient environmental air is drawn into the suction chamber 102 to combine or mix with the pressurized $O_2$ and generate the desired homogenous $O_2$ rich air mixture. The environmental air inlet 110 is also sized and otherwise configured to attach to an external filter 111 (see FIG. 16) for filtering dust, bacteria, viruses, and other such contaminants from the environmental air.

In the illustrated example, the body 100 also includes the secondary $O_2$ inlet 112 disposed between the primary $O_2$ inlet 108 and the outlet 114 and extends radially outward from the body 100. The secondary $O_2$ inlet 112 is oriented or otherwise configured to form an angle of approximately 50° (e.g., within manufacturing tolerances) with the body 100, however other angles and configurations are possible. In the illustrated example, the secondary $O_2$ inlet 112 can be connected to a secondary $O_2$ source (not shown) such that the concentration of pure $O_2$ gas in the homogenous $O_2$ gas mixture can be increased up to 100% $FiO_2$ That is, during operation, the secondary $O_2$ inlet can be used to supply additional $O_2$ into the suction chamber 102 to increase the % $FiO_2$ of the homogenous $O_2$ rich gas.

In various embodiments, and as best shown in FIGS. 2, 8, and 10A-10D, the primary $O_2$ inlet 108 includes a threaded inner surface 116 that threadably engages with the connector 200 to attach or otherwise connect the connector 200 to the body 100. The secondary $O_2$ inlet 112 includes a tapered tip 118 with multiple ridges 120 defined in the tip 118 and configured to grip or otherwise connect the oxygen delivery tube of the secondary $O_2$ source (not shown) to the secondary $O_2$ inlet 112. In the illustrated example, the secondary $O_2$ inlet 112 includes an inner surface 122 that defines a secondary $O_2$ channel that transports $O_2$ from the secondary $O_2$ source into the body 100.

Figure 16:
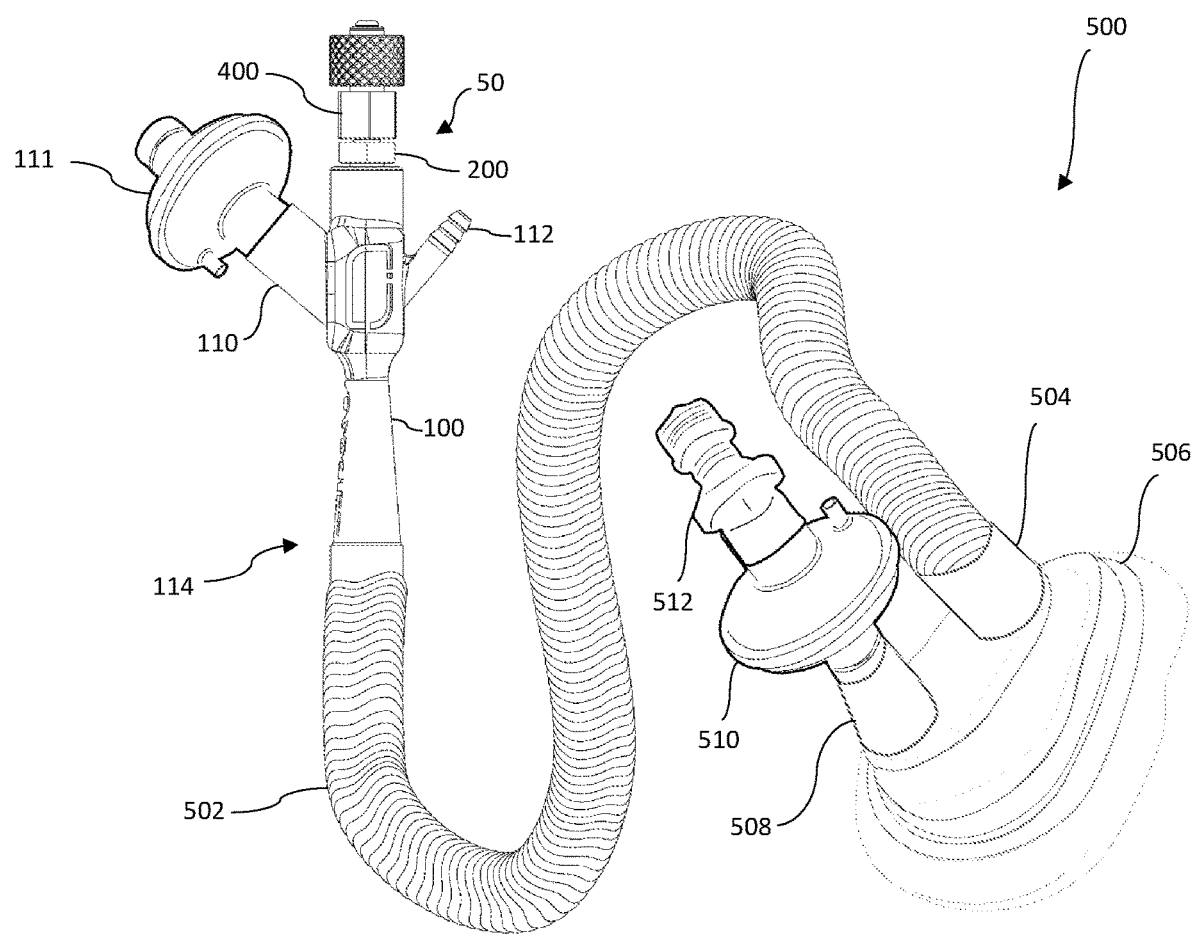
FIG. 16 is a perspective view of a CPAP breathing circuit including the flow generator of FIG. 1.

In the illustrated example, the environmental air inlet 110 includes an inner surface 124 that defines an inner channel for drawing in or otherwise entraining environmental air surrounding the flow generator 50 into the body 100. As best shown in FIG. 16, the filter 111 can be attached to the environmental air inlet 110 such that the filter 111 removes contaminants from the environmental air drawn into the body 100 via the environmental air inlet 110. In one non-limiting example the filter 111 is configured as a Viral/HEPA filter, however other types of filters are possible.

In the illustrated example, the primary $O_2$ inlet 108, environmental air inlet 110, and secondary $O_2$ inlet 112 are each connected to and in fluid communication with the suction chamber 102 of the flow generator body 100. As such, incoming air entering the body 100, via inlets 108, 110, and 112, is transported to the suction chamber 102 and flows into the mixing chamber 104 of the flow generator body 100. As discussed herein, the mixing chamber 104 is configured to provide an area within the body 100 that enables the incoming air (i.e., pressurized $O_2$ and entrained environmental air) to mix in the mixing chamber and form the homogenous $O_2$ rich air mixture. The homogenous $O_2$ rich air mixture then flows or is otherwise transported from the mixing chamber 104 into the diffuser chamber 106. As discussed herein, the diffuser chamber 106 is configured to induce a pressure recovery to the homogenous $O_2$ rich air mixture as the air flows from the mixing chamber 104, through the diffuser chamber 106, and out of the body 100 via the outlet 114.

As best shown in FIGS. 2, 4B, 5B, 11A-11E, and 15B, the flow generator 50 includes the connector 200 threadably engaged with the threaded inner surface 116 of the primary $O_2$ inlet. More specifically, the connector 200 includes a tool engagement portion 202 (e.g., hexagonal head for engagement with a wrench), and a connector body 204 extending from the tool engagement portion 202. In the illustrated example, the connector body 204 includes a threaded outer surface 206 defined along at least a portion of the connector body 204 and configured to thread into the threaded inner surface 116 of the primary $O_2$ inlet. In the illustrated example, the connector 200 also includes one or more inner surfaces 208 that define an interior chamber or void of the connector that includes an adapter receiver portion 210, a nozzle housing portion 212, and a nozzle outlet 214. In the illustrated example, the one or more inner surfaces 208 define a bore extending through the tool engagement portion 202 and into the adapter receiver portion 210. As such, the bore extending into the adapter receiver portion 210 defines a passageway such that at least a portion of the adapter 400 can be inserted into the connector and extend into the interior chamber of the connector 200. The nozzle housing portion 212 is configured to receive the removable nozzle 300 and position the at least a portion or the nozzle 300 within the interior chamber of the connector 200. The nozzle outlet 214 defines a passageway through the connector body 204 such that at least a portion of the nozzle 300 can extend out from the interior chamber of the connector 200.

In the illustrated example, the connector 200 is threaded or otherwise connected to the primary $O_2$ inlet 108 to position the nozzle 300 in the body 100. As best shown in FIGS. 11A-11E and 15B-15C, the connector 200 receives the nozzle 300 in the nozzle housing portion 212 such that at least a portion of the nozzle 300 extends out of the connector 200 via the nozzle outlet 214. More specifically, one or more inner surfaces 208 of the connector 200 define an inner threaded surface 216 of the adapter receiver portion 210 that threadably engages with a threaded outer surface 422 of the adapter 400. As such, during assembly of the flow generator 50, at least a portion of the adapter 400 extends into the interior chamber of the connector 200 and the threaded outer surface 422 of the adapter 400 threads into or otherwise meshes with the inner threaded surface 216 to fixedly connect the adapter to the connector 200.

As best shown in FIGS. 14A-14D, the primary nozzle 300 includes an adapter engagement surface 302, a nozzle body or hub 304 extending from the adapter engagement surface 302, and a nozzle tip 306 connected to and extending from the nozzle body 304. In the illustrated example, the nozzle 300 includes a first inner surface 308 that defines an interior void within the nozzle body 304 and a second inner surface 310 that defines a nozzle channel of nozzle tip 306. As such, inner surfaces 308 and 310 define a flow path through the nozzle 300. In the illustrated example, the interior void defined by the first inner surface 308 has a first diameter that is larger than a diameter of the nozzle channel defined by the second inner surface 310 such that the flow path reduces or constricts from the nozzle body 304 to the nozzle tip 306.

As discussed herein, the nozzle 300 is configured as a removable component of the flow generator 50 such that different nozzles can be installed into the flow generator 50 based on the desired output or other flow characteristics of the pressurized homogenous $O_2$ rich gas mixture generated by the flow generator 50. As such, different nozzles can be installed in the body 100 to optimize certain flow characteristics of the pressurized $O_2$ transported into the body 100. For example, the nozzle 300 is configured as a removeable fluid dispensing nozzle or needle selected from a range of different nozzle sizes (e.g., 15 to 22 gauge nozzles). As such, a certain nozzle can be selected as the nozzle 300 such that during operation of the flow generator 50 the nozzle 300 receives pressurized $O_2$ from the external $O_2$ supply. As the pressurized $O_2$ gas flows through the nozzle 300, the nozzle 300 causes an acceleration of incoming or driving flow to generate a sonic or supersonic condition of the pressurized $O_2$. In the illustrated example, the nozzle 300 is constructed out of a medical grade and biocompatible material such as stainless-steel, nickel-plated brass, plastic, polylactic acid (PLA), thermoplastic polyurethane (TPU) acrylonitrile butadiene styrene (ABS), polypropylene (PP), and polyvinylchloride (PVC), or other such medical grade material and the nozzle 300 is configured to withstand a variety of incoming air pressures (e.g., up to 100 psi).

As best shown in FIGS. 12A-12I, 13A-13D and 15A-15D, the adapter 400 includes a flow meter attachment portion 408, a tool engagement portion 410 (e.g., hexagonal head for engagement with a wrench), a first cylindrical portion 412 connected to and extending between the flow meter attachment portion 408 and the tool engagement portion 410, and a second cylindrical portion 414 connected to and extending from the tool engagement portion 410. The flow meter attachment portion 408 includes an O-ring 416 circumferentially surrounding the top of the flow meter attachment portion 408. The flow meter attachment portion 408 is configured to sealingly engage with the flow meter of the primary pressurized $O_2$ source. As such, the O-ring 416 helps to form a fluid tight seal between the flow meter attachment portion 408 and the flow meter. The flow meter attachment portion 408 also includes a retaining collar 418 configured to retain or otherwise maintain attachment of the rotatable knob 402 to the adapter 400.

In the illustrated example, the rotatable knob 402 is slidably attached to the adapter 400 such that the rotatable knob 402 can axially slide up and down along the first cylindrical portion 412 to align the rotatable knob 402 with the flow meter. The rotatable knob 402 includes a threaded inner surface 404 that defines a central opening extending between top and bottom surfaces of the rotatable knob 402. The threaded inner surface 404 defines a knob retainer 420 adjacent the bottom surface of the knob 402 that is configured to interact with the retaining collar 418 of the flow meter attachment portion 408 such that the rotatable knob 402 remains attached to the adapter 400.

Figure 15B:
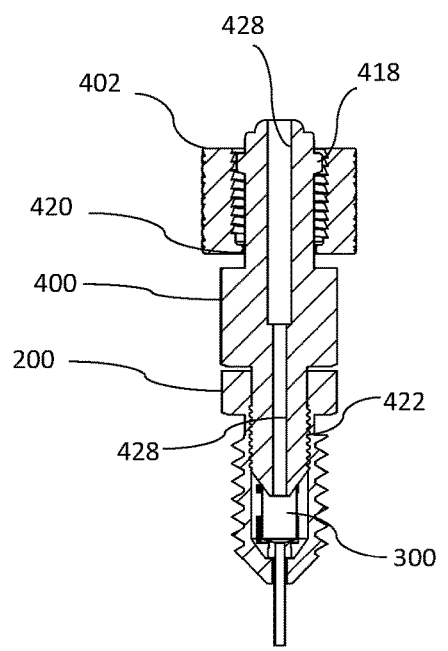
FIGS. 15A-15C show different perspective views and cross-sectional view of the connector, nozzle, and adapter assembly taken along line C-C.
Figure 15A:
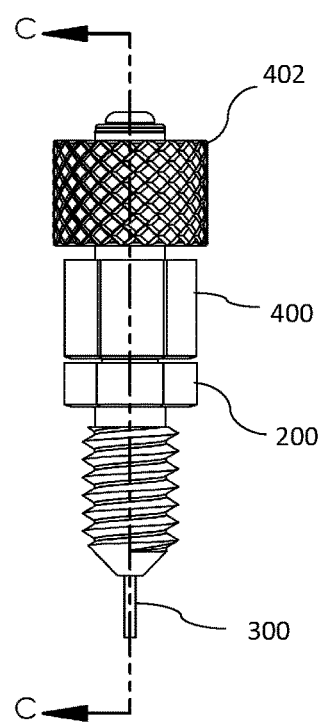
Figure 15C:
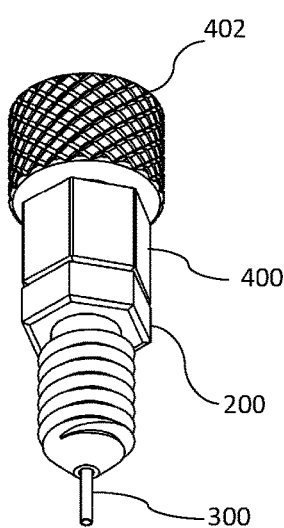

In the illustrated example, the second cylindrical portion 414 of the adapter 400 includes a threaded outer surface 422 and a nozzle engagement portion 424. As best illustrated in FIG. 15B, the threaded outer surface 422 of the second cylindrical portion 414 is configured to threadably engage the inner threaded surface 216 (see FIG. 11C) of the connector 200. As such, during the assembly of the flow generator 50, the tool engagement portion 410 of the adapter can be engaged by a tool such as a wrench or other tool to thread or otherwise tighten the adapter 400 into the connector 200. Additionally, the nozzle engagement portion 424 is configured to engage the nozzle 300 such that the adapter 400 is in fluid communication with the nozzle 300. More specifically, the nozzle engagement portion 424 includes a tapered tip or end 426 configured to extend into at least a portion of the nozzle body 304 and sealingly engage with the adapter engagement surface 302 of the nozzle 300 to form a fluid tight seal between the adapter 400 and the nozzle 300.

As best shown in FIGS. 12B and 15B, the adapter 400 includes multiple inner surfaces 428 that define an inner channel extending through the flow meter attachment portion 408, first cylindrical portion 412, tool engagement portion 410, and second cylindrical portion 414. As such, the inner surfaces 428 define a flow path through adapter 400 such that the adapter 400 acts as a conduit in fluid communication with the external pressurized $O_2$ source and the nozzle 300. In the illustrated example, the inner surfaces 428 define multiple different (e.g., larger, or smaller) diameters of the inner channel to constrict the flow path through the adapter 400. In one non-limiting example, the inner surfaces 428 define a first diameter dimension for a first section of the inner channel defined in the flow meter attachment portion 408, first cylindrical portion 412, and a portion of the tool engagement portion 410. The inner surfaces 428 define a second diameter for a second section of the inner channel defined in a portion of the tool engagement portion 410 and the second cylindrical portion 414. In the illustrated example, the first diameter is larger than the second diameter. As such, the inner surfaces 428 define a tapered or constricted inner channel along the length of the adapter 400. It will be understood that while the illustrated example shows a tapered inner channel defined in the adapter 400, other channel configurations are possible.

As discussed herein, the flow generator 50 is configured to securely attach or otherwise connect, via the adapter 400, to the flow meter of the pressurized primary $O_2$ source to supply pressurized $O_2$ to the flow generator 50. In the illustrated example, adapter 400 includes the rotatable knob 402 that is usable to connect (or disconnect) the flow generator 50 to the flow meter. In the illustrated example, the threaded inner surface 404 of the rotatable knob 402 is configured to threadably engage with the flow meter to connect the flow generator 50 to the primary pressurized $O_2$ gas supply. The rotatable knob 402 also includes a knurled outer surface 406 that enables a user to properly grip the rotatable knob 402 while connecting, and disconnecting, the flow generator 50 and the flow meter.

As best shown in FIG. 16, during operation the flow generator 50 can be incorporated into a breathing circuit 500 of a CPAP or other respiratory apparatus to generate a pressurized homogenous $O_2$ rich air mixture. In the illustrated example, the filter 111 is suitably connected to the environmental air inlet 110. The filter 111 is configured as a viral/HEPA filter configured to filter dust, bacteria, viruses, or other such airborne contaminants from the environmental air drawn into the flow generator 50. The outlet 114 of the flow generator 50 is connected to a first end of a respiratory tube 502. A second end of the respiratory tube 502 is connected to an inlet 504 of a CPAP mask 506 that fits over the nose and/or mouth of a patient. Accordingly, the respiratory tube 502 and CPAP mask 506 transports the pressurized homogenous $O_2$ rich airflow generated by the flow generator 50 to the patient. The CPAP mask 506 also includes an outlet 508 connected to a second filter 510 and a variable PEEP valve 512. In the illustrated example, the filter 510 is configured as a viral/HEPA filter that filters the exhaled air of the patient wearing the CPAP mask 506 prior to the exhaled air being released into the surrounding environment and mixing in with the environmental air.

FIGS. 17A, 17B, 18A and 18B illustrate a second embodiment of the flow generator of the disclosure, identified as flow generator 1050. It should be appreciated that the flow generator 1050 is similar to the flow generator 50 illustrated in FIGS. 1-5B and 16, except for the differences discussed herein. As such, the same element numbers are used to illustrate similar or common elements shared between flow generator 1050 and flow generator 50. Elements of the flow generator 1050 that correspond to but have differences from flow generator 50 use element numbers that correspond to the element numbers of flow generator 50 with an additional "1" at the beginning of the element labels (e.g., 100 becomes 1100, 400 becomes 1400, and the like). It should also be appreciated that the general operation of the flow generator 1050 is the same as the general operation of the flow generator 50, except as discussed herein. It should therefore be appreciated that the disclosure discussed herein with respect to flow generator 50 applies to the flow generator 1050, except where such disclosure is inconsistent with the elements of flow generator 1050, as discussed herein.

In the illustrated example, the flow generator 1050 includes a flow generator body 1100 (sometimes referred to herein as body for brevity), the nozzle 300 disposed in the body 1100, and an adapter 1400 sealingly engaged with the nozzle 300 and suitably connected to the body 1100. In the illustrated example, the adapter 1400 includes a rotatable knob 1402 suitably connected to the adapter 1400 and configured to removably connect the flow generator 1050 to a flow meter or regulator (not shown) connected to an external pressurized $O_2$ supply (not shown) or other such pressurized gas supply.

Figure 18A:
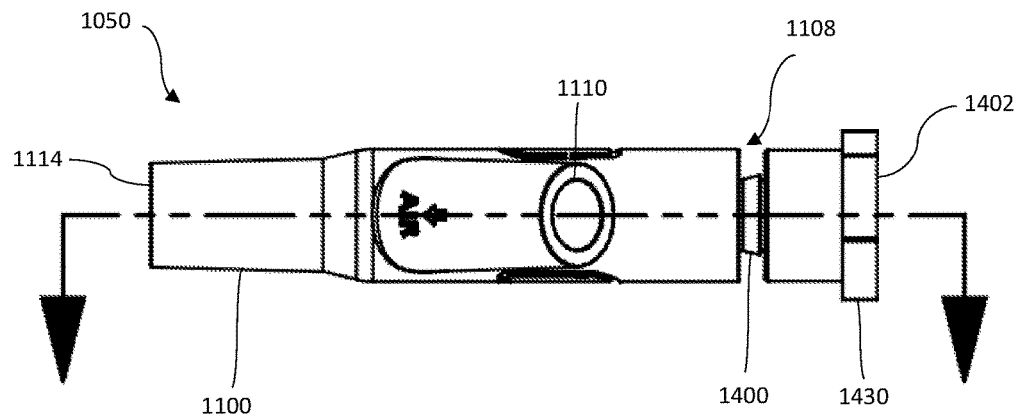
FIG. 18A is a top view of the flow generator of FIG. 17A.
Figure 18B:
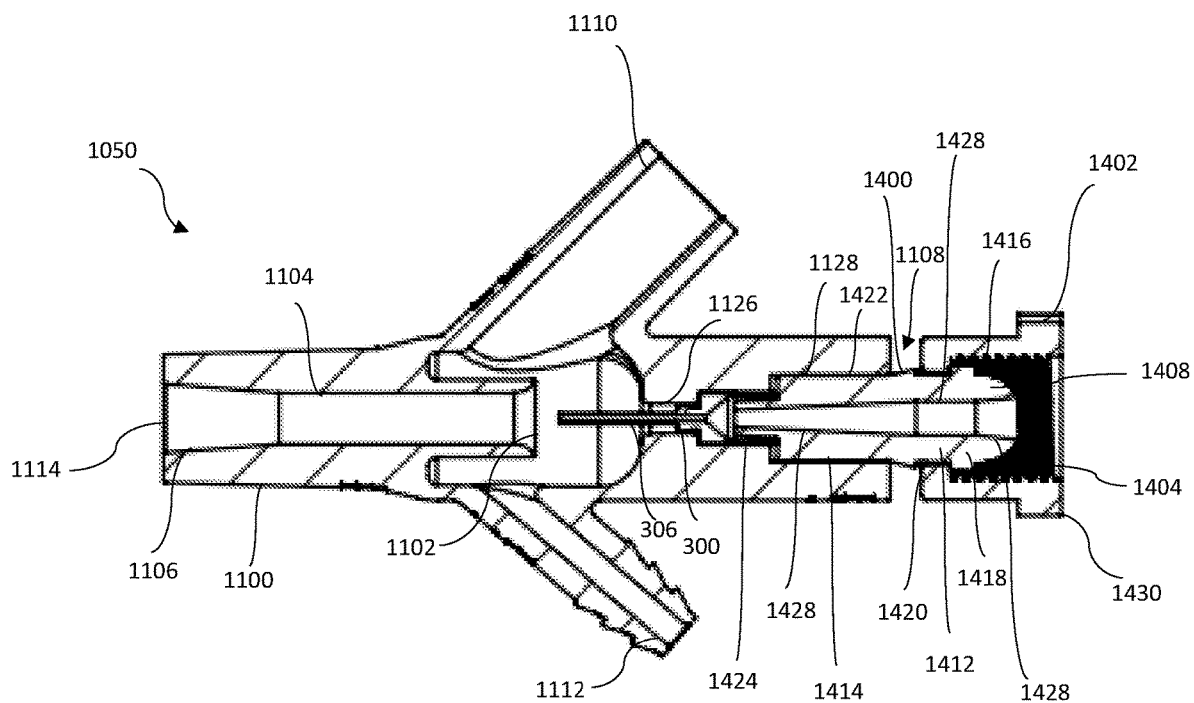
FIG. 18B is a cross-sectional view of the flow generator of FIG. 18A taken along line A-A.

As best shown in the cross-sectional view of FIG. 18B, the body 1100 includes multiple inner surfaces (not labeled for clarity) that define a first inner chamber 1102 (sometimes referred to herein as a suction chamber), a second inner chamber 1104 (sometimes referred to herein as a mixing chamber) in fluid communication with the first inner chamber 1102, and a third inner chamber 1106 (sometimes referred to herein as a diffuser chamber) in fluid communication with the second inner chamber 1104. In the illustrated example, the plurality of inner surfaces of the body 1100 are configured such that the inner chambers 1102, 1104, and 1106 are in fluid communication with each other and define a fluid flow pathway through the body 1100.

In the illustrated example, the outer and inner surfaces of the body 1100 also define a first inlet 1108 (sometimes referred to herein as the primary $O_2$ inlet) at a first end of the body 1100, a flow generator outlet 1114 (sometimes referred to herein as the outlet) at a second end of the body 1100, a second inlet 1110 (sometimes referred to herein as the environmental air inlet) disposed between the primary $O_2$ inlet 1108 and the outlet 1114, and a third inlet 1112 (sometimes referred to herein as the secondary $O_2$ inlet) disposed between the primary $O_2$ inlet 1108 and the outlet 1114. However, while the illustrated example of the flow generator 1050 includes three inlets and one outlet, it will be understood that the body can be configured to include a different number of inlets and/or outlets (e.g., a fewer or greater number).

In the illustrated example, the primary $O_2$ inlet 1108, environmental air inlet 1110, and secondary $O_2$ inlet 1112 are each connected to and in fluid communication with the suction chamber 1102 of the body 1100. As such, a primary source of pressurized $O_2$ (sometimes referred to herein as the driving gas flow) flows into the body 1100 via the primary $O_2$ inlet 1108. The velocity of the incoming pressurized $O_2$ generates a low-pressure region in the suction chamber 1102 that causes the flow generator 1050 to draw or otherwise entrain surrounding environmental air into the flow generator 1050. More specifically, the low-pressure region generated in the suction chamber 1102 causes the flow generator 1050 to draw surrounding environmental air into the suction chamber 1102, via the environmental air inlet 1110. As such, the incoming pressurized $O_2$ and entrained environmental air combine with each other in the suction chamber 1102 and mix with one another in the mixing chamber 1104 to form the pressurized homogenous $O_2$ rich air mixture. As discussed herein, the pressurized homogenous $O_2$ air mixture continues to flow from the mixing chamber 1104, through the diffusion chamber 1106, and flow out of the body 1100 via the outlet 1114.

In the illustrated example, the inner surfaces (not labeled for clarity) of the body 1100 define a nozzle receiver portion 1126 and an adapter receiver portion 1128 of the primary $O_2$ inlet 1108. The nozzle receiver portion 1126 is configured to receive and position the nozzle 300 such that the nozzle body 304 is housed or otherwise received in the nozzle receiver portion 1126 and the nozzle tip 306 extends through the nozzle receiver portion 1126 and into the suction chamber 1102 of the body 1100.

Figure 17A:
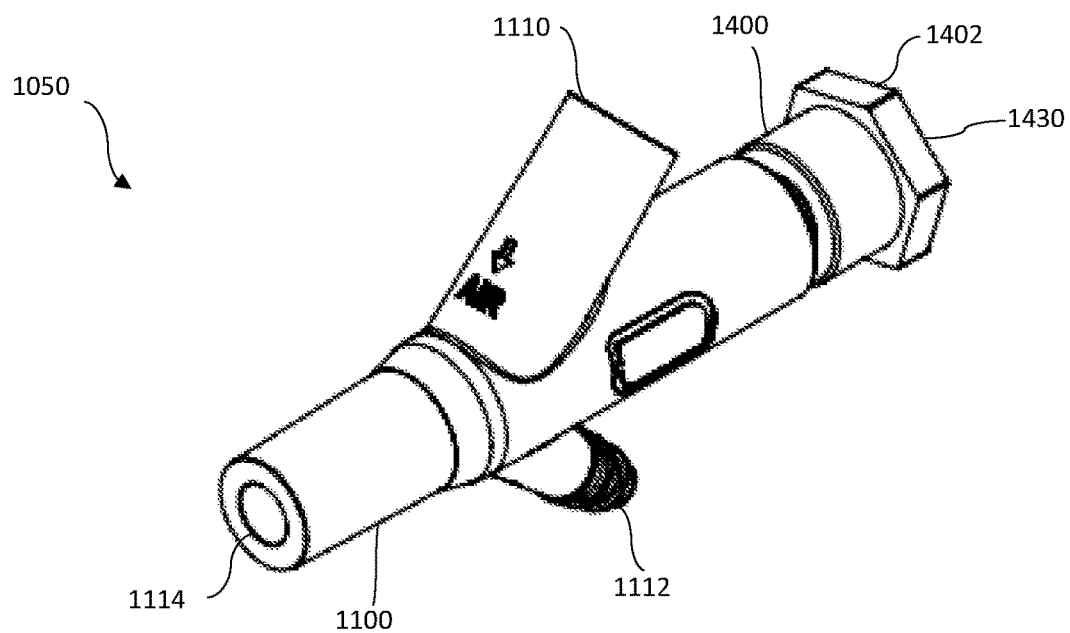
FIG. 17A is a perspective view of another embodiment of the flow generator of the disclosure.
Figure 17B:
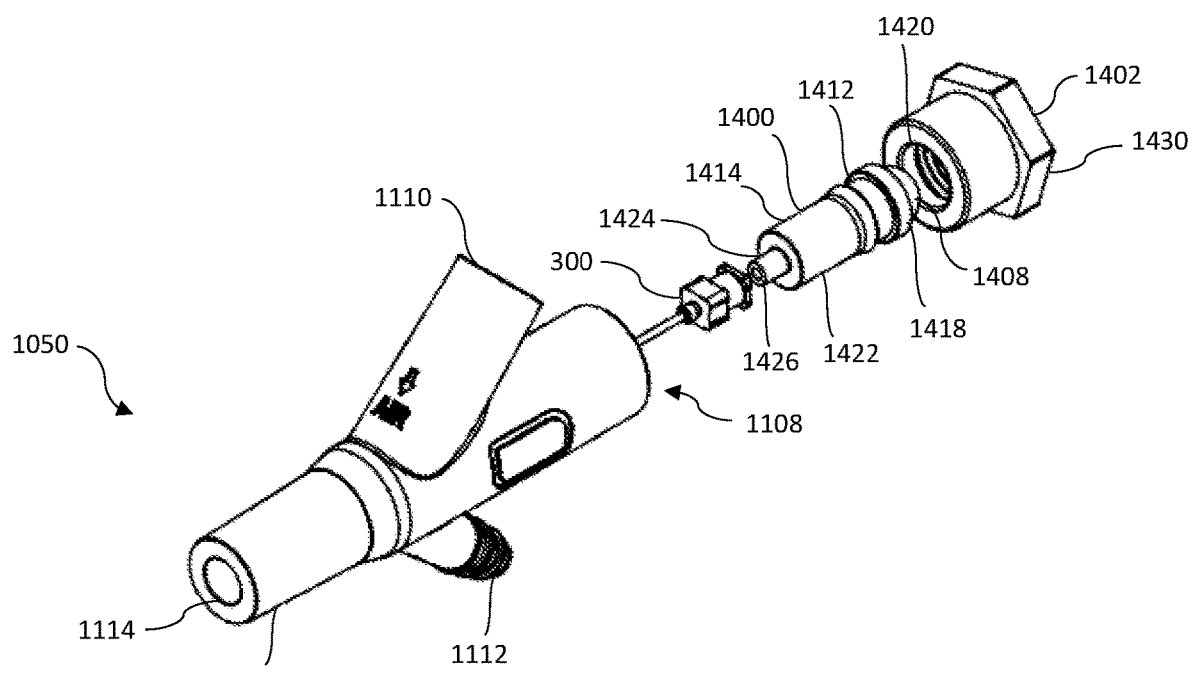
FIG. 17B is an exploded perspective view of the flow generator of FIG. 17A.

As best shown in FIGS. 17B and 18B, the adapter 1400 includes a flow meter attachment portion 1408, a first cylindrical portion 1412 and a second cylindrical portion 1414. The first cylindrical portion 1412 is connected to and extends from the flow meter attachment portion 1408. The second cylindrical portion 1414 is connected to and extends from the first cylindrical portion 1412. As such, the first cylindrical portion 1412 is disposed between the flow meter attachment portion 1408 and the second cylindrical portion 1414. The flow meter attachment portion 1408 includes an 0-ring 1416 circumferentially surrounding the adapter 1400 and is configured to sealingly engage with the flow meter (not shown) of the primary pressurized $O_2$ source. As such, the O-ring 1416 helps to form a fluid tight seal between the flow meter attachment portion 1408 and the flow meter. The flow meter attachment portion 1408 also includes a retaining collar 1418 configured to retain or otherwise maintain attachment of the rotatable knob 1402 to the adapter 1400.

In the illustrated example, the rotatable knob 1402 is slidably attached to the adapter 1400 such that the rotatable knob 1402 can axially slide up and down along the first cylindrical portion 1412 to align the rotatable knob 1402 with the flow meter. The rotatable knob 1402 includes a threaded inner surface 1404 that defines a central opening extending between top and bottom surfaces of the rotatable knob 1402. The threaded inner surface 1404 defines a knob retainer 1420 adjacent the bottom surface of the knob 1402 that is configured to interact with the retaining collar 1418 of the flow meter attachment portion 1408 such that the rotatable knob 1402 remains attached to the adapter 1400. In the illustrated example, the rotatable knob 1402 also includes a tool engagement portion 1430 (e.g., hexagonal head for engagement with a wrench). The tool engagement portion 1430 of the adapter 1400 can be engaged by a tool such as a wrench or other tool to thread or otherwise tighten or otherwise connect the adapter 1400 to the external primary $O_2$ supply.

In the illustrated example, the second cylindrical portion 1414 includes an outer sealing surface 1422 such that the adapter 1400 is connected to or otherwise fixedly attached to the inner surfaces that define the adapter receiver portion 1128 of the primary $O_2$ inlet 1108 via an interference fit, however other attachment methods of the adapter 1400 to the body 1100 are possible. For example, the inner surfaces of the body 1100 can define a threaded inner surface (not shown) of the primary $O_2$ inlet 1108. The outer sealing surface 1422 of the second cylindrical portion 1414 can define a threaded outer surface (not shown) configured to thread into the adapter receiver portion 1128 of the primary $O_2$ inlet 1108.

As best illustrated in FIGS. 17B and 18B, the adapter 1400 further includes a third cylindrical portion 1424 (sometimes referred to herein as a nozzle engagement portion) extending from the second cylindrical portion 1414. In the illustrated example, the nozzle engagement portion 1424 is configured to engage the nozzle 300 such that the adapter 1400 is in fluid communication with the nozzle 300. More specifically, the nozzle engagement portion 1424 includes a tapered tip or end 1426 configured to extend into at least a portion of the nozzle body 304 and the nozzle engagement portion 1424 sealingly engages with the adapter engagement surface 302 of the nozzle 300 to form a fluid tight seal between the adapter 1400 and the nozzle 300.

As best shown in FIG. 18B, the adapter 1400 includes one or more inner surfaces 1428 that define an inner channel extending through the flow meter attachment portion 1408, first cylindrical portion 1412, second cylindrical portion 1414, and third cylindrical portion 1424. As such, the adapter 1400 acts as a conduit in fluid communication with the external pressurized $O_2$ source and the nozzle 300 that transports the pressurized 02 into the flow generator 1050. In the illustrated example, the one or more inner surfaces 1428 define multiple different (e.g., larger, or smaller) diameters of the inner channel. In one non-limiting example, the one or more inner surfaces 1428 define at least two or more different diameters along the inner channel such that the inner channel is tapered or narrowed along the length of the adapter 1400. It will be understood that while the illustrated example shows a tapered inner channel defined in the adapter 1400, other inner channel configurations are possible.

This section lists some advantages of disclosed embodiments. Additional advantages of the disclosed embodiments should be apparent from reading the other sections of the specification.

The flow generator of this disclosure does not require any electricity and/or electrical components to operate. Rather, the flow generator is configured to use the energy stored in the external pressurized $O_2$ source to produce the homogenous $O_2$ rich air flow mixture. As such, the flow generator of the disclosure is more economical to operate and may exhibit improved reliability over more complex devices. The flow generator of the disclosure is configured to generate a positive airway pressure by using the flow generator output and the residual flow after patient inhalation. As such, the flow generator of the disclosure may use lower amounts of incoming pressurized $O_2$ to generate a constant flow rate of a homogenous $O_2$ rich air mixture at a required positive pressure and $FiO_2$.

The flow generator of the disclosure is compatible with conventional flow meters and regulators used with pressurized $O_2$ cylinders as well as with wall-mounted flow meters and regulators connected to central $O_2$ supply lines in medical facilities. Using a 15 LPM flow rate provided by these flow meters, the flow generator of the disclosure can generate adjustable flow rates up to 120 LPM, depending on the PEEP value and inflow rate of the incoming primary pressurized $O_2$. When the flow generator of the disclosure is connected to CPAP masks and/or helmets, the flow generator can produce a PEEP pressure range between 5 $cmH_2O$ to 20 $cmH_2O$.

During operation, the flow generator of the disclosure uses a relatively small inflow (e.g., up to 15 LPM) of pressurized $O_2$ to generate an increased flow (e.g., up to 120 LPM) of pressurized homogenous $O_2$ rich air by creating a low-pressure region in the mixing chamber when inflowing pressurized $O_2$ through the primary nozzle. Furthermore, this pressure gradient generated in the flow generator of the disclosure causes surrounding environmental or room air to be drawn or otherwise entrained into the mixing chamber via the environmental air inlet. Typically, environmental air surrounding the flow generator is composed of approximately 21% $O_2$ and is mixed with the pure pressurized $O_2$ transported into the suction chamber via the primary inlet. As such, the total output flow rate of the flow generator of the disclosure is increased while reducing the overall $FiO_2$%. In cases where a higher $FiO_2$% is desired, the secondary $O_2$ inlet can be connected to a secondary pressurized $O_2$ source to combine with the primary pressurized $O_2$ source and supply up to an additional 65 LPM of pure pressurized $O_2$ to the flow generator of the disclosure. By regulating or otherwise controlling the inflow of the secondary pressurized $O_2$ delivered via the secondary $O_2$ inlet, the $FiO_2$% can be as high as 100% while the generated flow and PEEP pressure change is minimal because such parameters are largely dependent on the inflow of the primary pressurized $O_2$. Put differently, the flow generator of the disclosure can provide 65 LPM of pressurized $O_2$ rich air at 100% $FiO_2$ by controlling the inflow of the pressurized $O_2$ through the primary inlet. To provide an increased flow rate up to 120 LPM at 100% $FiO_2$ of pressurized $O_2$ rich air, an additional inflow of pressurized $O_2$ (e.g., up to 105 LPM) can be provided to the flow generator via the secondary inlet.

The flow generator of the disclosure includes a body configured to generate the homogenous $O_2$ rich air flow to avoid an uneven pressure distribution of the air flow mixture output by the flow generator. To accomplish this, after mixing the inflow of pressurized $O_2$, and environmental air in the mixing chamber, the air mixture is transported from the mixing chamber to the diffusion chamber. The diffusion chamber is tapered along the length of the chamber such that the diffusion chamber has a gradually increasing diameter. That is, the diameter of the diffusion chamber is smallest in the diffusion chamber portion adjacent the mixing chamber and the diameter of the diffusion chamber is largest in the diffusion chamber portion adjacent the outlet 114.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any equivalent thereof.

Various embodiments of a flow generator for generating an oxygen rich air flow have a body including a first inlet, a second inlet, an outlet, and one or more inner surfaces that define a first inner chamber in fluid communication with the first inlet and the second inlet, a second inner chamber in fluid communication with the first inner chamber, and a third inner chamber in fluid communication with the second chamber and the outlet of the body. A connector disposed in the first inlet and connected to the body, the connector including one or more inner surfaces that define a connector inner chamber and a connector bore extending into the inner chamber. A nozzle disposed within at least a portion of the connector inner chamber and extending into the first inner chamber, and an adapter extending through the connector bore into the connector inner chamber and sealingly engaged to the nozzle to form a fluid tight flow path through the adapter and the nozzle. The adapter is configured to connect to and receive a first pressurized oxygen supply from a primary oxygen source and transport the first pressurized oxygen supply into the nozzle.

In one such embodiment, the second inner chamber has a first chamber diameter that is constant along a length of the second inner chamber.

In another such embodiment, a first end of the third inner chamber has a second chamber diameter equal to the first chamber diameter and a second end of the third inner chamber has a third chamber diameter larger than the second chamber diameter such that the third inner chamber has an increasing diameter between the first end and the second end of the third inner chamber.

In another such embodiment, the nozzle comprises a nozzle body and a nozzle tip connected to and extending from the nozzle body, and wherein the connector inner chamber is configured to house the nozzle body of the nozzle.

In another such embodiment, the first inlet includes a threaded inner surface.

In another such embodiment, wherein the connector includes a tool engagement portion, and a connector body extending from the tool engagement portion, and wherein the connector body has a threaded outer surface configured to threadably engage with the threaded inner surface of the first inlet.

In another such embodiment, the one or more inner surfaces of the connector define an adapter receiver portion, a nozzle housing portion, and a nozzle outlet in the interior chamber of the connector.

In another such embodiment, the adapter receiver portion includes a threaded inner surface, and wherein the adapter includes a threaded outer surface configured to threadably engage with the threaded inner surface of the adapter receiver portion.

In another such embodiment, the nozzle includes a nozzle body and a nozzle tip extending from the nozzle body, and wherein the nozzle housing portion of the connector receives the nozzle body, and the nozzle tip extends through the nozzle outlet of the connector.

In another such embodiment, the nozzle is configured as a removable component selected from a range of 15 gauge to 22 gauge nozzles.

In another such embodiment, the adapter includes a flow meter attachment portion, a tool engagement portion, a first cylindrical portion connected to and extending between the flow meter attachment portion and the tool engagement portion, and a second cylindrical portion connected to and extending from the tool engagement portion.

In another such embodiment, the adapter includes a rotatable knob slidably connected to the first cylindrical portion and configured to removably connect the flow meter adapter portion to a flow meter of an external oxygen supply.

In another such embodiment, the adapter includes one or more inner surfaces that define an inner channel extending through the flow meter attachment portion, the first cylindrical portion, the tool engagement portion, and the second cylindrical portion, and wherein the one or more inner surfaces define a flow path through adapter.

In another such embodiment, the one or more inner surfaces define a first diameter and a second diameter of the inner channel, and wherein the first diameter is larger than the second diameter such that the inner channel forms a tapered inner channel.

In another such embodiment, the body comprises a third inlet connected to and in fluid communication with the first chamber.

In another such embodiment, the third inlet is configured to connect to and receive a second pressurized oxygen supply from a secondary oxygen source and transport the second pressurized oxygen supply into the first chamber.

In another such embodiment, the body is fabricated as a unitary structure including the first inlet the second inlet, the third inlet, and the outlet.

In another such embodiment, wherein the body is fabricated using a 3D printed process, and wherein the unitary structure is formed from a biocompatible material selected from one of a polylactic acid (PLA), a thermoplastic polyurethane (TPU), an acrylonitrile butadiene styrene (ABS), a polypropylene (PP), or a polyvinylchloride (PVC).

In another such embodiment, the nozzle is fabricated out of a biocompatible material selected from one of a stainless-steel, a nickel-plated brass, a plastic, polylactic acid (PLA), a thermoplastic polyurethane (TPU) an acrylonitrile butadiene styrene (ABS), a polypropylene (PP), or a polyvinylchloride (PVC).

In another such embodiment, the second inlet is configured to connect to an external filter.

Various embodiments of a flow generator for generating an oxygen rich air flow have a body including a first inlet, a second inlet, an outlet, and one or more inner surfaces that define a first inner chamber in fluid communication with the first inlet and the second inlet, a second inner chamber in fluid communication with the first inner chamber, and a third inner chamber in fluid communication with the second chamber and the outlet of the body. A nozzle disposed within at least a portion of the body and extending into the first inner chamber. The flow generator further includes an adapter disposed in the first inlet of the body and sealingly engaged to the nozzle to form a fluid tight flow path through the adapter and the nozzle. The adapter is configured to connect to and receive a first pressurized oxygen supply from a primary oxygen source and transport the first pressurized oxygen supply into the nozzle.

In one such embodiment, the one or more inner surfaces of the body define a nozzle receiver portion and an adapter receiver portion in the first inlet of the body.

In another such embodiment, the nozzle receiver portion is configured to receive and position the nozzle within the first inlet of the body.

In another such embodiment, a nozzle body of the nozzle is housed in the nozzle receiver portion and a nozzle tip of the nozzle extends through the nozzle receiver portion and into the first inner chamber of the body.

In another such embodiment, the adapter includes a flow meter attachment portion, a first cylindrical portion connected to and extending from the flow meter attachment portion, and a second cylindrical portion connected to and extending from the first cylindrical portion.

In another such embodiment, the second cylindrical portion includes an outer sealing surface configured to connect the adapter to the adapter receiver portion of the body via an interference fit.

In another such embodiment, the second cylindrical portion includes an outer threaded surface configured to threadably engage with an inner threaded surface of the adapter receiver portion.

In another such embodiment, the adapter further includes a third cylindrical portion extending from the second cylindrical portion and configured to engage with the nozzle.

In another such embodiment, the third cylindrical portion includes a tapered tip configured to extend into at least a portion of a nozzle body of the nozzle, and the third cylindrical portion sealingly engages with an adapter engagement surface of the nozzle to form a fluid tight seal between the adapter and the nozzle.

In another such embodiment, the adapter includes one or more inner surfaces that define an inner channel extending through the flow meter portion, the first cylindrical portion, the second cylindrical portion, and the third cylindrical portion.

In another such embodiment, the one or more inner surfaces define a plurality of different diameters along the inner channel such that the inner channel is tapered along a length of the adapter.

What is claimed is:

1. A flow generator for generating an oxygen rich air flow, the flow generator comprising:
    a body including a first inlet, a second inlet extending radially outward from the body at a first acute angle, a third inlet extending radially outward from the body at a second acute angle different than the first acute angle, an outlet, and one or more inner surfaces that define a first inner chamber in fluid communication with the first inlet, the second inlet, and the third inlet, a second inner chamber in fluid communication with the first inner chamber, and a portion of the second inner chamber is extended into the first inner chamber, and a third inner chamber in fluid communication with the second inner chamber and the outlet of the body;
    a connector disposed in the first inlet and connected to the body, the connector including one or more inner surfaces that define a connector inner chamber and a connector bore extending into the connector inner chamber;
    a nozzle disposed within at least a portion of the connector inner chamber and extending into the first inner chamber of the body to define a gap between the nozzle and the second inner chamber of the body; and
    an adapter extending through the connector bore into the connector inner chamber and sealingly engaged to the nozzle to form a fluid tight flow path through the adapter and the nozzle, wherein the adapter is configured to connect to and receive a first pressurized oxygen supply from a primary oxygen source and transport the first pressurized oxygen supply into the nozzle.

2. The flow generator of claim 1, wherein the second inner chamber of the body has a first chamber diameter that is constant along a length of the second inner chamber.

3. The flow generator, of claim 2, wherein a first end of the third inner chamber has a second chamber diameter equal to the first chamber diameter and a second end of the third inner chamber has a third chamber diameter larger than the second chamber diameter such that the third inner chamber has an increasing diameter between the first end and the second end of the third inner chamber.

4. The flow generator of claim 1, wherein the nozzle comprises a nozzle body and a nozzle tip connected to and extending from the nozzle body, and wherein the connector inner chamber is configured to house the nozzle body of the nozzle.

5. The flow generator of claim 1, wherein the first inlet includes a threaded inner surface.

6. The flow generator of claim 5, wherein the connector includes a tool engagement portion, and a connector body extending from the tool engagement portion, and wherein the connector body has a threaded outer surface configured to threadably engage with the threaded inner surface of the first inlet.

7. The flow generator of claim 1, wherein the one or more inner surfaces of the connector define an adapter receiver portion, a nozzle housing portion, and a nozzle outlet in the interior chamber of the connector.

8. The flow generator of claim 7, wherein the adapter receiver portion includes a threaded inner surface, and wherein the adapter includes a threaded outer surface configured to threadably engage with the threaded inner surface of the adapter receiver portion.

9. The flow generator of claim 7, wherein the nozzle includes a nozzle body and a nozzle tip extending from the nozzle body, and wherein the nozzle housing portion of the connector receives the nozzle body, and the nozzle tip extends through the nozzle outlet of the connector.

10. The flow generator of claim 9, wherein the nozzle is configured as a removable component selected from a range of 15 gauge to 22 gauge nozzles.

11. The flow generator of claim 1, wherein, the adapter includes a flow meter attachment portion, a tool engagement portion, a first cylindrical portion connected to and extending between the flow meter attachment portion and the tool engagement portion, and a second cylindrical portion connected to and extending from the tool engagement portion.

12. The flow generator of claim 11, wherein the adapter includes a rotatable knob slidably connected to the first cylindrical portion and configured to removably connect the flow meter adapter portion to a flow meter of an external oxygen supply.

13. The flow generator of claim 11, wherein the adapter includes one or more inner surfaces that define an inner channel extending through the flow meter attachment portion, the first cylindrical portion, the tool engagement portion, and the second cylindrical portion, and wherein the one or more inner surfaces define a flow path through adapter.

14. The flow generator of claim 13, wherein the one or more inner surfaces define a first diameter and a second diameter of the inner channel, and wherein the first diameter is larger than the second diameter such that the inner channel forms a tapered inner channel.

15. The flow generator of claim 1, wherein the third inlet is configured to connect to and receive a second pressurized oxygen supply from a secondary oxygen source and transport the second pressurized oxygen supply into the first chamber.

16. The flow generator of claim 1, wherein the body is fabricated as a unitary structure including the first inlet, the second inlet, the third inlet, and the outlet.

17. The flow generator of claim 16, wherein the body is fabricated using a 3D printed process, and wherein the unitary structure is formed from a biocompatible material selected from one of a polylactic acid (PLA), a thermoplastic polyurethane (TPU), an acrylonitrile butadiene styrene (ABS), a polypropylene (PP), or a polyvinylchloride (PVC).

18. The flow generator of claim 1, wherein the nozzle is fabricated out of a biocompatible material selected from one of a stainless-steel, a nickel-plated brass, a plastic, polylactic acid (PLA), a thermoplastic polyurethane (TPU) an acrylonitrile butadiene styrene (ABS), a polypropylene (PP), or a polyvinylchloride (PVC).

19. The flow generator of claim 1, wherein the second inlet is configured to connect to an external filter.

20. The flow generator of claim 1, wherein the outlet of the flow generator is operably connected to a first end of a respiratory tube, and wherein a second end of the respiratory tube is operably connected to a CPAP mask configured to deliver the oxygen rich air flow generated by the flow generator.

* * * * *